(12) United States Patent
Gao et al.

(10) Patent No.: US 11,697,755 B2
(45) Date of Patent: Jul. 11, 2023

(54) DEGRADABLE TAGS FOR DEPTH CORRELATION MUD LOGGING

(71) Applicant: ARAMCO SERVICES COMPANY, Houston, TX (US)

(72) Inventors: Chengzhe Gao, Blacksburg, VA (US); Shitong Sherry Zhu, Waban, MA (US); Marta Antoniv, Cambridge, MA (US); Nouf AlJabri, Dhahran (SA)

(73) Assignees: ARAMCO SERVICES COMPANY, Houston, TX (US); SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 17/375,417

(22) Filed: Jul. 14, 2021

(65) Prior Publication Data
US 2022/0017805 A1 Jan. 20, 2022

Related U.S. Application Data

(60) Provisional application No. 63/051,548, filed on Jul. 14, 2020.

(51) Int. Cl.
*C09K 8/08* (2006.01)
*E21B 49/00* (2006.01)
*G01N 33/28* (2006.01)

(52) U.S. Cl.
CPC .............. *C09K 8/08* (2013.01); *E21B 49/005* (2013.01); *G01N 33/2882* (2013.01)

(58) Field of Classification Search
CPC .................................................... E21B 49/005
See application file for complete search history.

(56) References Cited

U.S. PATENT DOCUMENTS

| 4,142,853 | A | * | 3/1979 | Terada ............... D06P 5/005 8/539 |
| 1,342,222 | A | | 8/1982 | Alekhin et al. |
| 5,955,401 | A | | 9/1999 | Liao |
| 8,729,253 | B2 | * | 5/2014 | Buchanan ............ C08B 3/16 536/64 |
| 2010/0304418 | A1 | | 12/2010 | Moussavi et al. |
| 2011/0210064 | A1 | * | 9/2011 | Cheng ............... D01F 6/42 210/500.33 |
| 2014/0054039 | A1 | * | 2/2014 | Chang ............... C09K 8/885 166/292 |
| 2017/0088698 | A1 | * | 3/2017 | Collins ............... D01F 2/28 |
| 2017/0130117 | A1 | | 5/2017 | Gordon et al. |
| 2018/0128096 | A1 | | 5/2018 | Cox |
| 2018/0237688 | A1 | | 8/2018 | Duenckel et al. |
| 2018/0298274 | A1 | | 10/2018 | Zhao |
| 2018/0298277 | A1 | | 10/2018 | Borrell et al. |
| 2019/0211652 | A1 | | 7/2019 | Camp et al. |
| 2019/0360326 | A1 | * | 11/2019 | Deville ............... E21B 49/005 |
| 2019/0382653 | A1 | | 12/2019 | Borrell et al. |

FOREIGN PATENT DOCUMENTS

| CA | 2807827 | A1 | 6/2013 |
| CN | 103409130 | B | 9/2015 |
| CN | 110041900 | A | 7/2019 |
| WO | 2016/176381 | A1 | 11/2016 |
| WO | 2019/058098 | A1 | 3/2019 |

OTHER PUBLICATIONS

International Search Report and Written Opinion issued in Application No. PCT/US2021/041573, dated Nov. 4, 2021 (16 pages).
Zhang et al.; "Synthesis of cellulose benzoates under homogeneous conditions in an ionic liquid". Cellulose; vol. 16; Oct. 12, 2008; pp. 299-308 (10 pages).
Hamdaoui et al.; "Preparation and characterization of cellulose p-phenylbenzoate by two-step synthesis from microcrystalline and kraft cellulose", Polymer Bulletin; vol. 72; No. 12; Jul. 9, 2015; pp. 3031-3042 (12 pages).
C. E. Frazier and W. G. Glasser; "Intramolecular Effects in Cellulose Mixed Benzyl Ethers Blended with Poly (e-caprolactone)". Journal of Applied Polymer Science; vol. 58; Issue 6; pp. 1063-1075 (13 pages).

* cited by examiner

*Primary Examiner* — Silvana C Runyan
(74) *Attorney, Agent, or Firm* — Osha Bergman Watanabe Burton LLP

(57) ABSTRACT

Degradable polymer additives are provided. The degradable polymer additives include a tracer functional group that is bonded to a base polymeric component by a hydrolysable covalent bond. The base polymeric component is a polysaccharide. The tracer functional group is selected from the group comprising a halogen-containing functional group, a substituted heterocyclic aromatic group, and combination thereof. A method utilizing the degradable polymeric additives in an altered drilling fluid is provided. Such a method includes introducing the altered drilling fluid into a wellbore and recovering an associated wellbore cutting from a depleted drilling fluid.

12 Claims, 26 Drawing Sheets

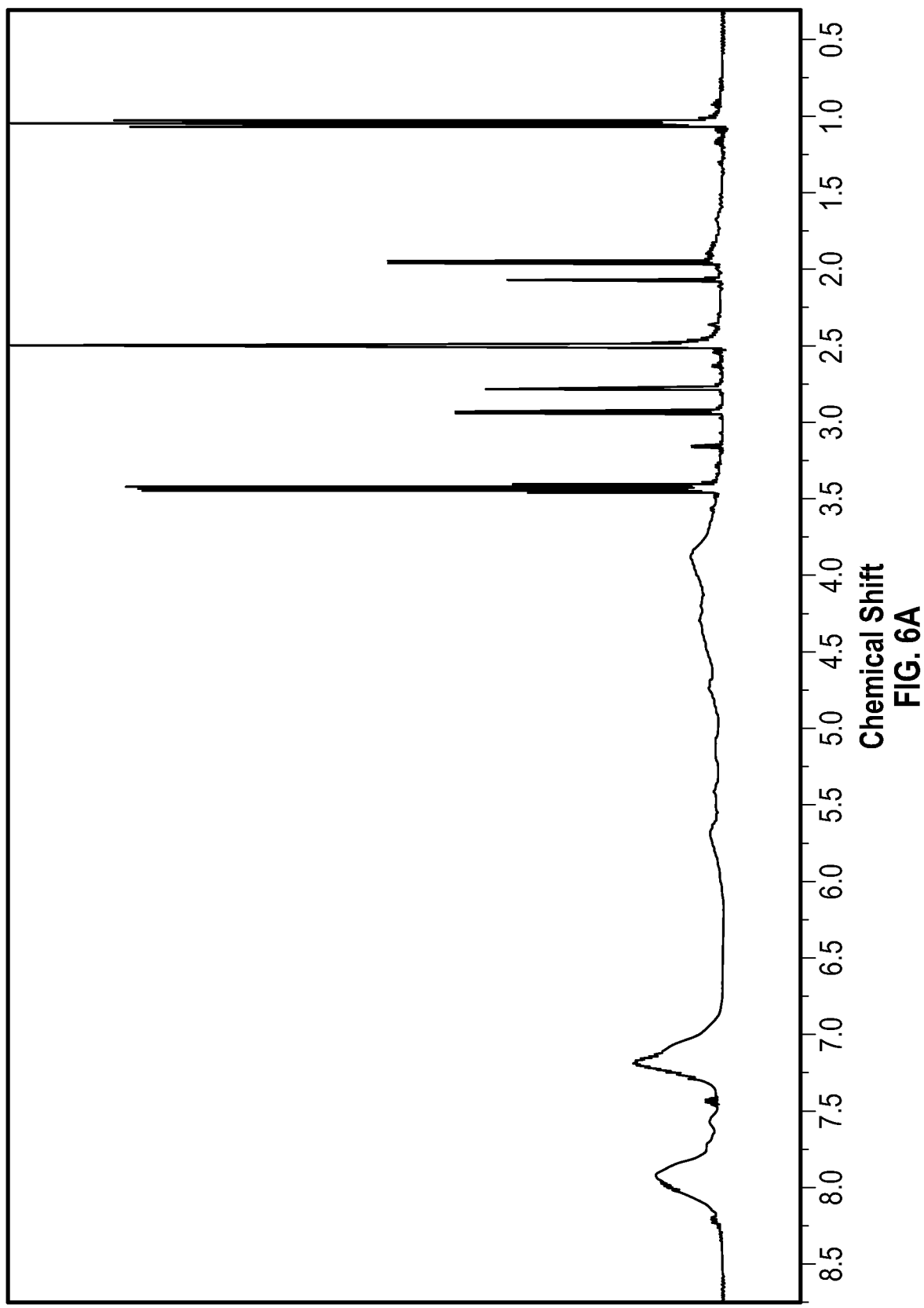

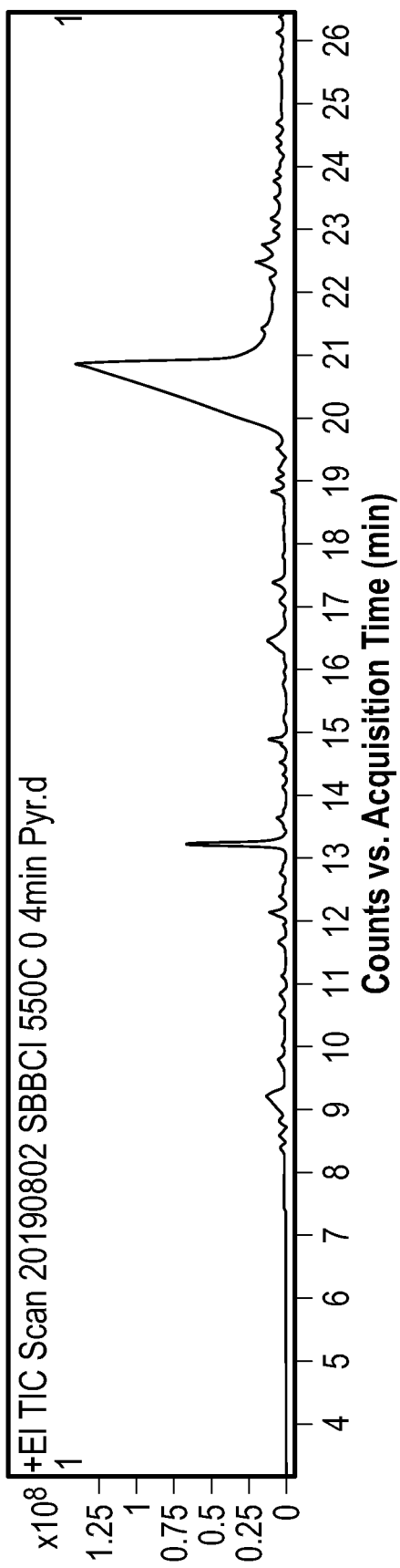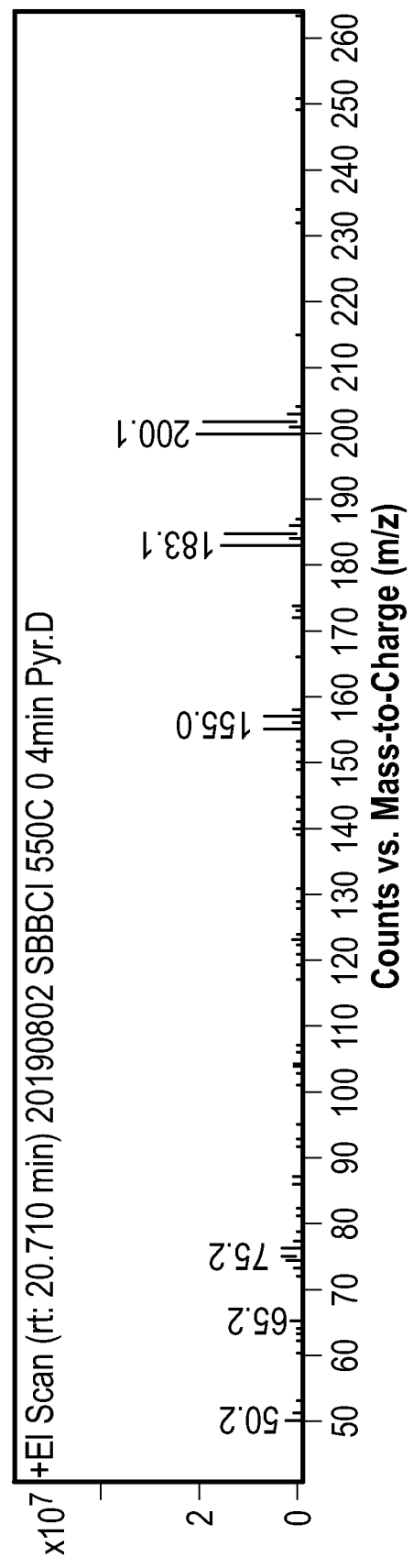
FIG. 11A
FIG. 11B

DEGRADABLE TAGS FOR DEPTH CORRELATION MUD LOGGING

CROSS-REFERENCE TO RELATED APPLICATIONS

This application claims priority from U.S. Patent Application No. 63/051,548, filed Jul. 14, 2020, the contents of which are incorporated by reference in their entirety.

BACKGROUND

Hydrocarbon-bearing formations ("reservoirs") may be complex subterranean formations containing multiple fluid phases. Tracers provide a means of elucidating the structure of the subterranean formation by injecting water-soluble molecules, such as fluorescent dyes, to detect fluid pathways and velocities of the fluid movement. The tracers can be injected at various locations, such as through an injection well, and then detected in the various output locations, such as a production well.

Tracers may also be used for "tagging" cuttings during drilling operations. A tracer binds itself to the cutting when it contacts the formation material surface of the cutting. The tracer then acts as a marker or "tag" associated with the depth from which the cuttings originated. This can be accomplished by introducing the tracer into the flow of the drilling fluid called "mud" for a short period yet in highly concentrated amounts.

Integrating the direct petrophysical characterization of drill cuttings into mud logging practices has the potential to support or displace logging while drilling (LWD). Mud logging is particularly promising in applications, such as underbalanced drilling with coiled tubing. In such activities, the hole size prohibits the use of LWD tools; therefore, real-time mud logging would be greatly beneficial.

SUMMARY

This Summary is provided to introduce a selection of concepts that are further described in the Detailed Description. This Summary is not intended to identify key or essential features of the claimed subject matter, nor is it intended to be used as an aid in limiting the scope of the claimed subject matter.

In one aspect, embodiments disclosed relate to degradable polymer additives. The degradable polymer additives include a tracer functional group that is bonded to a base polymeric component by a hydrolysable covalent bond. The base polymeric component is a polysaccharide. The tracer functional group is selected from the group comprising a halogen-containing functional group, a substituted heterocyclic aromatic group, and combination thereof.

In another aspect, embodiments disclosed relate altered drilling fluids. The altered drilling fluid combines a base fluid with the aforementioned degradable polymer additive.

In another aspect, one or more embodiments relate to a method of using the degradable polymer additive. The method includes introducing an amount of the degradable polymeric additive into a drilling fluid to form an altered drilling fluid. The method also includes introducing the altered drilling fluid into a wellbore. The method also includes recovering an associated wellbore cutting from a depleted drilling fluid. The method includes detecting the presence of the degradable polymeric additive associated with the associated wellbore cutting. The degradable polymer additive is similar to the aforementioned degradable polymer additive.

Other aspects and advantages of the claimed subject matter will be apparent from the following description and the appended claims.

BRIEF DESCRIPTION OF DRAWINGS

FIG. 6A depicts the $^1$H NMR spectra of starch 4-fluorobenzoate (SFB), which is a degradable polymeric additive, according to one or more embodiments.

FIGS. 11A-B show the pyrolysis gas chromatography-mass spectrometry (Py GC-MS) analysis and the mass spectra of starch 4-bromobenzoate (SBB), which is a degradable polymeric additive, according to one or more embodiments.

DETAILED DESCRIPTION

Figure 1A:
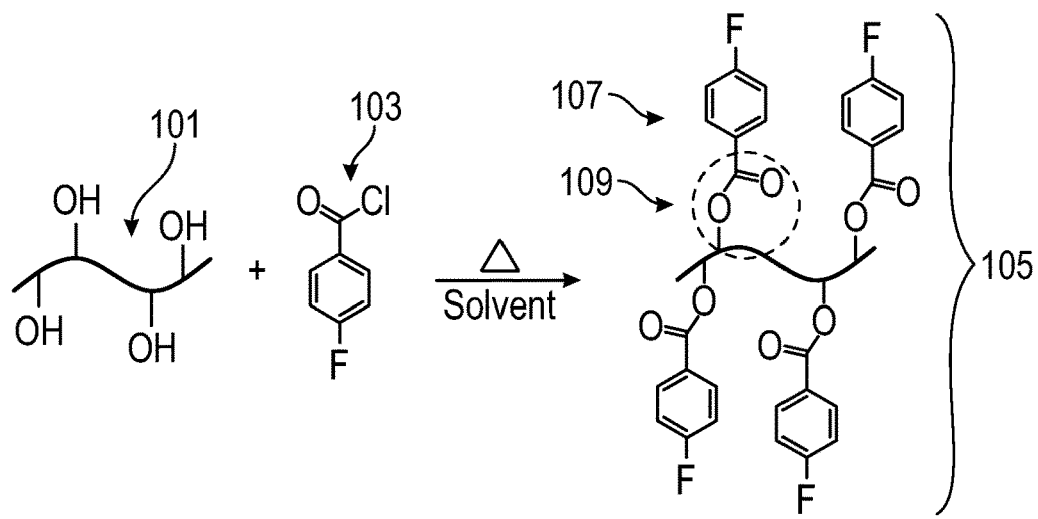
FIGS. 1A-C are schematic illustrations depicting the preparation of several degradable polymeric additives according to one or more embodiments.

The use of chemical tracers to mark wellbore cuttings, however, has its downsides. Traditional chemical tracers, some of which will not bond to the surface of a cutting, over time accumulate or "build up" in the drilling mud. Drilling mud is recycled once the cuttings are removed and basic chemical and physical properties of the mud are adjusted. There is no operation or means at the surface for eliminating or purging chemical tracers from the drilling mud. Therefore, to continue to use chemical tracers to mark cuttings, one must use either a greater tracer concentration or several tracers with different tags to overcome the detection noise generated from the accumulated tracers in the drilling mud.

Another significant issue in mud logging, however, involves issues around subpar quality of the tagging and depth association. Phenomena such as wellbore mud hydraulics, poor hole cleaning, and inaccurate knowledge of the return-trip lag time of the cuttings back up the annulus may all contribute to the uncertainty. For example, return-trip lag time is usually assumed by known physical structure of the wellbore annulus; however, wellbore caving and the shuffling of cuttings during their trip to the surface may result in mischaracterization of the depth where the chemical tracer bonded with the cutting. Long horizontal sections pose additional concerns. In horizontal sections of well, gravitational debris accumulation, different hydraulics, and hole cleaning operations are more problematic, which adds to the potential uncertainty. When the mud return trip lasts approximately thirty minutes, it is common to have depth uncertainties of ±6 meters (20 feet) or more. Finally, in any situation, human error in the labelling of the collected cuttings can also be a factor.

Embodiments in accordance with the present disclosure generally relate to degradable polymeric additives that may be used in oilfield applications, including as a tracer in subterranean reservoirs. Generally, the degradable polymeric additives of one or more embodiments may include a base polymeric component, such as a polysaccharide or a synthetic polymer that is covalently bonded to a tracer functional group via a hydrolysable covalent bond. The tracer functional group is derived by reacting a tracer functional compound with the base polymeric component to form the degradable polymer additive with the hydrolysable covalent bond. The tracer functional group is configured such that it may be detected within one or more fluids, such as a drilling fluid, used within a wellbore or a reservoir and, therefore, may be traceable.

The degradable polymeric additives of one or more embodiments may advantageously serve as "degradable tracers". The degradable polymeric additives, which degrade after a certain period under downhole conditions, form the base polymeric component and the tracer functional compound, in a reversable chemical reaction. This reversable reaction prevents the accumulation of the degradable polymeric additives in the drilling mud. Preventing accumulation limits the amount of detection noise, circumvents the need for developing as many signatures, and may eliminate some forms of error—both machine and human—from accidentally assigning a depth to a legacy signal. The degradable polymeric additives of one or more embodiments may advantageously reduce the depth uncertainty of mud logging measurements by preventing confounding effects of multiple detectable signals, especially when different tracers are used in close proximity to one another (time) during sensitive drilling operations.

Degradable Polymeric Additives

In one or more embodiments, the degradable polymeric additives may include a base polymeric component covalently bonded via a hydrolysable covalent bond to a tracer functional group.

Figure 1B:
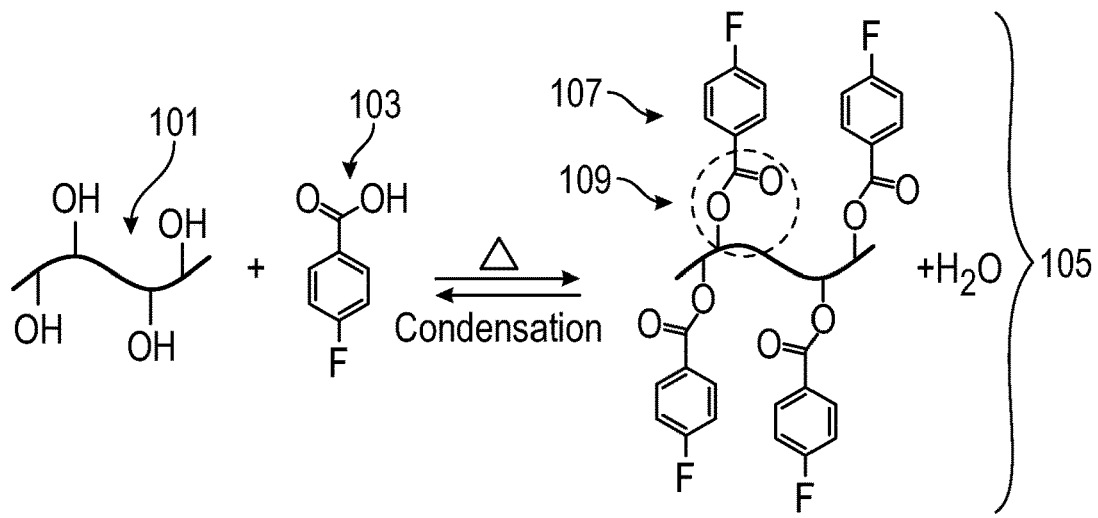
Figure 1C:
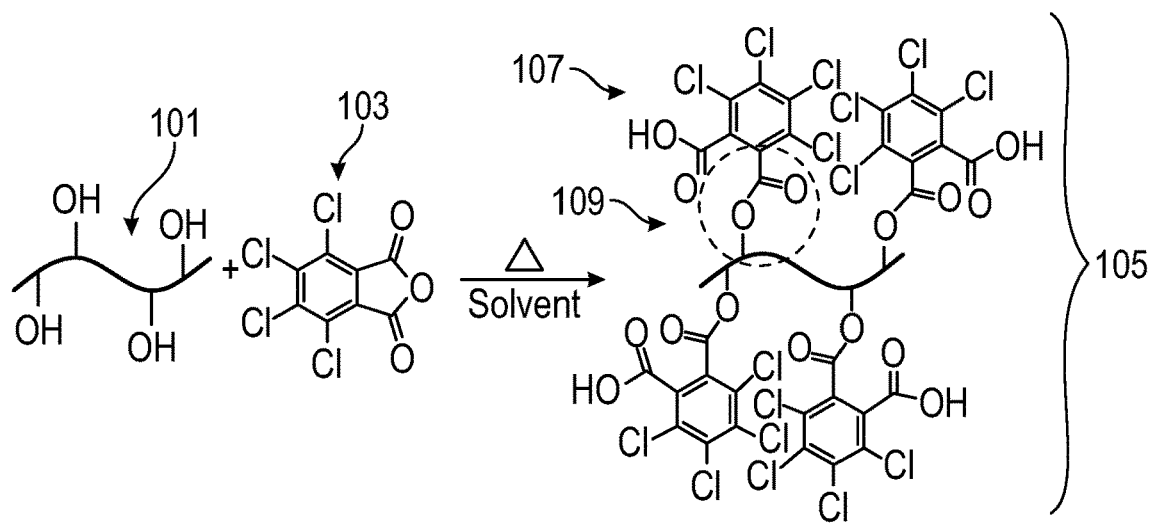

FIGS. 1A-C are schematic illustrations depicting the preparation of several degradable polymeric additives according to one or more embodiments. Shown separately in each of FIGS. 1A-C, base polymeric component 101 and tracer functional compound 103 react through various reactions schemes (substitution, condensation) to form several degradable polymeric additives 105, which are reaction products. Each degradable polymeric additive 105 is shown with several tracer functional groups 107 covalently bonded to and part of the degradable polymeric additive 105. Each degradable polymeric additive 105 is shown with hydrolysable covalent bond 109, in each case an ester linkage, associated with the tracer functional group 107.

Base Polymeric Component

The base polymeric component of one or more embodiments may be any polymer that is suitable for functionalization. The base polymeric component of one or more embodiments may comprise homopolymers, copolymers, interpolymers, or mixtures thereof. The base polymeric component may comprise a commercially available polymer. The base polymeric component has properties suitable for its intended application, such as acting as being compatible with the drilling mud, acting as a foundation material for conveying tracer functional groups downhole, and assisting in the coupling to cuttings.

In one or more embodiments, the base polymeric component may comprise one or more of a naturally occurring polymer. In one or more embodiments, the base polymeric component may be a polysaccharide. Examples of a useful polysaccharide include, but are not limited to, starch, a derivatized starch, guar gum, cellulose, a derivatized cellulose, xanthan gum, chitin, dextran, scleroglucan, chitosan, gellan gum, arabic gum, alginate, curdlan, hyaluronic acid, lentinan, levan, pullulan, schizophyllan, stewartan, succinoglycan, welan, and combinations thereof.

In the context of this application, "derivative" and similar terms means that the base material has been chemically modified; however, its base functionality has not been so altered as to render the material ineffective for its intended purpose as a degradable polymeric additive.

In one or more embodiments, the base polymeric component of one or more embodiments may be a non-naturally occurring or synthetic polymer. In one or more embodiments, the synthetic polymer may be one or more selected from the group consisting of polyvinyl alcohols, modified polyvinyl alcohols, and combinations thereof.

The naturally occurring polymer and the synthetic polymer of one or more embodiments may have reactive functionalities, such as a hydroxyl functional group, a carboxylic acid functional group, an amine functional group, an aldehyde functional group, an acyl chloride functional group, an acid anhydride functional group, an epoxide functional group, a thiol functional group, an alkene functional group, and an alkyne functional group. The base polymeric component may have one or more reactive functionalities in number. The base polymeric component may have one or more reactive functionalities in type. These reactive functionalities enable covalent bonding with a tracer functional compound. Upon reaction, the degradable polymeric additive forms with tracer functional groups attached by hydrolysable covalent bond.

In one or more embodiments, the base polymeric component may have a weight average molecular weight ($M_w$) in a range of from about 1,000 to 300,000 g/mol (grams per mole). For example, the polymeric component may have a $M_w$ that is in a range having a lower limit of any of one of 1,000, 5,000, 10,000, 15,000, 25,000, 50,000, and 100,000 g/mol to an upper limit of any one of 50,000, 100,000, 150,000, 200,000, 250,000, and 300,000 g/mol, where any lower limit can be used in combination with any mathematically-compatible upper limit.

In one or more embodiments, the base polymeric component may have a degree of polymerization in a range of from about 5 to 3,000. For example, the base polymeric component may have a degree of polymerization that is in a range having a lower limit of any of one of 5, 10, 20, 50, 100, 500, 1,000, 1,500, and 2,000, to an upper limit of any one of 100, 250, 500, 750, 1,000, 1,500, 2,000, 2,500, and 3,000, where any lower limit can be used in combination with any mathematically-compatible upper limit.

In one or more embodiments the base polymeric component may have a density that is equal to or greater than 1.00 g/cm$^3$ (grams per cubic centimeter). For example, the polymeric component may have a density that is in a range having a lower limit of any of one of 1.00, 1.10, 1.20, 1.30, and 1.40 g/cm$^3$ to an upper limit of any one of 1.40, 1.50, 1.60, 1.70, 1.80, and 2.00 g/cm$^3$, where any lower limit can be used in combination with any mathematically-compatible upper limit.

Tracer Functional Compound and Derived Tracer Functional Group

In one or more embodiments, any chemical can be used as a tracer functional compound for creating a degradable polymeric additive if the derived tracer functional group may be readily detected from one or more other materials present in a subterranean formation. One of ordinary skill in the art will appreciate, with the benefit of this disclosure, that the suitability of a tracer functional compound and its associated tracer functional group for a given application is dependent upon the other components present in this application.

The tracer functional group in accordance with one or more embodiments may be readily detected by one or more analytical techniques known to one of ordinary skill in the art, including, but not limited to, chromatographic, mass spectrometric, absorption spectroscopic, and electrochemical techniques. In one or more embodiments, the tracer functional group may be readily detected by one or more of gas chromatography-mass spectrometry (GC-MS), liquid chromatography-mass spectrometry (LC-MS), pyrolysis gas chromatography-mass spectrometry (Py GC-MS), high performance liquid chromatography (HPLC), IR (infra-red) spectroscopy, UV (ultra violet)-vis spectroscopy, fluorescence emission spectroscopy, Raman spectroscopy, thermogravimetric analysis (TGA), nuclear magnetic resonance (NMR), and combinations thereof. A person of skill in the art will appreciate the appropriate device and its use in detecting the presence of a tracer functional group.

In one or more embodiments, the tracer functional group may be readily detected by Py GC-MS. The tracer functional group may have a distinctive isotopic pattern or an unambiguous mass pattern in the GC-MS spectrum that is revealed upon testing. In one or more embodiments, the tracer functional group may contain one or more atoms of the group comprising fluorine, chlorine, bromine, sulfur, selenium, boron, and combinations thereof. In one or more embodiments, the tracer functional group in accordance with the present disclosure may contain chromophores or dyes that give known yet unique spectrum. In one or more embodiments, the tracer functional group in accordance with the present disclosure may contain one or more of fluorine, chlorine, and bromine.

The tracer functional compound of one or more embodiments may include at least one reactive functionality to enable attachment to the base polymeric component. One or more embodiments, the tracer functional compound may contain, prior to reaction with the base polymeric component, a hydroxyl functional group, a carboxylic acid functional group, an acyl chloride functional group, an acid anhydride functional group, an epoxide functional group, and combinations thereof.

The tracer functional group of the degradable polymeric additive of one or more embodiments may be readily detected by one or more of the previously described analytical techniques. In one or more embodiments, the tracer functional group may be detected in an a concentration of about 100 parts per million by weight (ppmw) or less, such as 50 ppmw, such as 10 ppmw, such as 5 ppmw, such as 1 ppmw, such as 0.5 ppmw, and such as 0.1 ppmw.

In one or more embodiments, the tracer functional group may be coupled or connected to the degradable polymeric additive by a hydrolysable covalent bond. Examples of a hydrolysable covalent bond may include, but are not limited to, an ester, amide, ether, thioether, or thioester bond. For example, in FIGS. 1A-C, the hydrolysable covalent bond 109 is an ester group.

The tracer functional group is derived from the tracer functional compound. The tracer functional compound may be halogenated or include a substituted heterocyclic aromatic compounds, or combinations thereof; therefore, the tracer function group may be a halogen-containing functional group, a substituted heterocyclic aromatic group, or combinations thereof.

Useful tracer functional compounds may include, but are not limited to, pyridine, pyran, thiopyran, azepine, quinolone, isoquinoline, carbazole, acridine, dibenzazepine thiophene, indole, isoindole, and derivatives thereof; and combination thereof. The tracer functional compound may include halogenated aromatic compounds, such as benzoic and naphthalic acids, salts, anhydrides, and derivatives thereof, and combinations thereof.

The tracer functional compound of one or more embodiments may be, prior to esterification, a benzene-containing molecule having a structure consistent with one of formulae (I), (II), (III), and (IV):

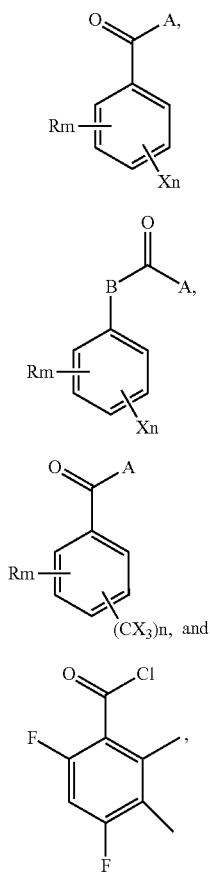

where A is a hydroxyl group or a chlorine atom; B is an alkyl or aromatic group; R is one of a hydrogen atom, an alkyl group, a hydroxyl group, a carboxylic acid group, an amine, an ether, a glycol, and an amide group; m is an integer in a range of from 0 to 4; X is a fluorine, chlorine, or bromine atom; and n is an integer in a range of from 1 to 5.

The tracer functional compound of one or more embodiments may be, prior to esterification, a naphthene-containing molecule having a structure consistent with one of formulae (V), (VI), (VII), and (VIII):

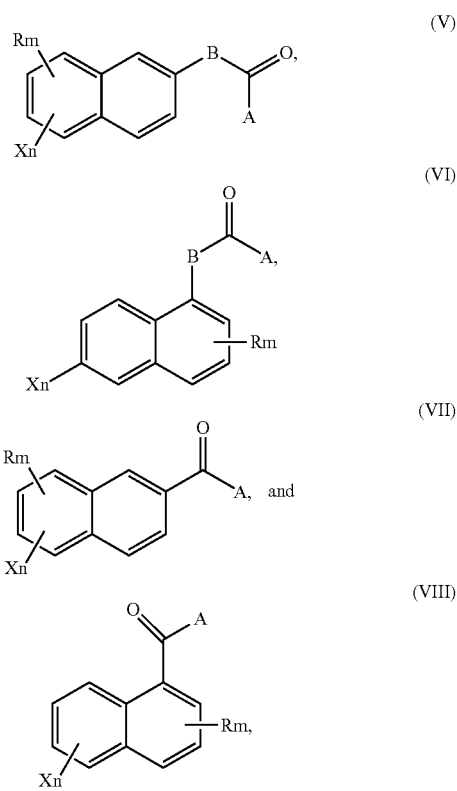

where A is a hydroxyl group or a chlorine atom; B is an alkyl or aromatic group; R is one of a hydrogen atom, an alkyl group, a hydroxyl group, a carboxylic acid group, an amine, an ether, a glycol, or an amide group; m is an integer in a range of from 0 to 6; X is a fluorine, chlorine, or bromine atom; and n is an integer in a range of from 1 to 7.

The tracer functional compound of one or more embodiments may be, prior to esterification, an isoquinoline-containing molecule having a structure consistent with formula (IX):

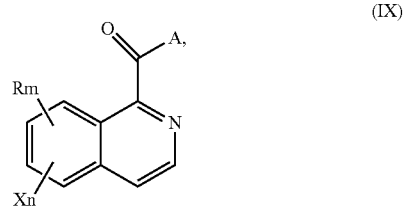

where A is a hydroxyl group or a chlorine atom; R is one of a hydrogen atom, an alkyl group, a hydroxyl group, a carboxylic acid group, an amine, an ether, a glycol, or an amide group; m is an integer in a range of from 0 to 5; X is a fluorine, chlorine, or bromine atom; and n is an integer in a range of from 1 to 6.

The tracer functional compound of one or more embodiments may be, prior to esterification, a phthalic anhydride-containing molecule having a structure consistent with formula (X):

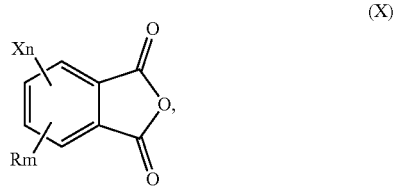

(X)

where R is one of a hydrogen atom, an alkyl group, a hydroxyl group, a carboxylic acid group, an amine, an ether, a glycol, and an amide group; m is an integer in a range of from 0 to 3; X is a fluorine, chlorine, or bromine atom; and n is an integer in a range of from 1 to 4.

The tracer functional compound of one or more embodiments may be, prior to esterification, a benzoic anhydride-containing molecule having a structure consistent with formula (XI):

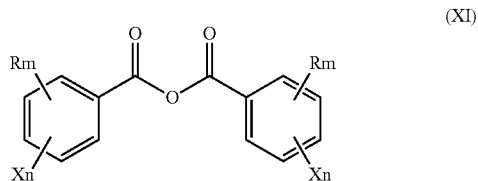

(XI)

where R is one of a hydrogen atom, an alkyl group, a hydroxyl group, a carboxylic acid group, an amine, an ether, a glycol, and an amide group; m is an integer in a range of from 0 to 4; X is a fluorine, chlorine, or bromine atom; and n is an integer in a range of from 1 to 5.

Properties of the Degradable Polymeric Additives

In one or more embodiments, a degradable polymeric additive may contain the tracer functional groups in an amount ranging from 1 to 100 mole percent (mol %), such as in a range of from about 30 to 100 mol %, of the reactive functionalities of the base polymeric component (for example, hydroxy groups for forming degradable ester bonds or amine groups for forming degradable amide bonds) available before converting the base polymeric component into the degradable polymeric additives. For example, in the reactions shown in FIGS. 1A-C, 100 mol % of the reactive functionalities (hydroxy groups) of the base polymer component are converted into the tracer functional groups for the degradable polymeric additives. For example, the degradable polymeric additives may contain tracer functional groups in an amount in a range of a lower limit of any one of 1, 5, 10, 20, 30, 40, and 50 mol % to an upper limit of any one of 40, 50, 60, 70, 80, 90, and 100 mol %, where any lower limit can be used in combination with any mathematically-compatible upper limit. One of ordinary skill in the art will appreciate, with the benefit of this disclosure, that the mol % tracer functional groups of total combined functional groups comprising the degradable polymeric additive depends on many factors, such as the nature of the tracer functional group, the reactive functionality of the base polymeric component, and the base polymeric component itself.

In one or more embodiments, the degradable polymeric additives may have a weight average molecular weight ($M_w$) in a range of from about 1,000 to 400,000 g/mol. For example, the degradable polymeric additives may have a $M_w$ that is in an amount in a range of a lower limit of any one of 1,000, 5,000, 10,000, 15,000, 25,000, 50,000, and 100,000 g/mol to an upper limit of any of 50,000, 100,000, 150,000, 200,000, 250,000, 300,000 and 400,000 g/mol, where any lower limit can be used in combination with any mathematically-compatible upper limit.

In one or more embodiments the degradable polymeric additives may have a density that is equal to or greater than 1.00 g/cm$^3$. For example, the degradable polymeric additives may have a density that is of an amount ranging from a lower limit of any of 1.00, 1.10, 1.20, 1.30, and 1.40 g/cm$^3$ to an upper limit of any of 1.40, 1.50, 1.60, 1.70, 1.80, and 2.00 g/cm$^3$, where any lower limit can be used in combination with any mathematically-compatible upper limit.

The degradable polymeric additives of one or more embodiments may be soluble or dispersible in water or in organic solvents. In one or more embodiments, the degradable polymeric additives may form colloids in aqueous, organic, or combinations thereof, fluids. The particle size of the degradable polymeric additives may be in a range of from about 10 nm (nanometers) to 300 microns (micrometers).

In one or more embodiments, the degradable polymeric additives may be degraded by cleaving the bond between the polymeric component and the tag. As shown in FIGS. 1A-C, the reaction is reversable between the degradable polymeric additive, the base polymeric component, and tracer functional compound. The cleavage may be achieved through a variety of reactions, including, but not limited to, hydrolysis, aminolysis, reduction, thermolysis, electrolysis, and combinations thereof. The degradable polymeric additives may be degraded, that is hydrolysable, under acidic, alkaline, or a change from acidic to alkaline, or a change from alkaline to acidic, conditions.

In one or more embodiments, the degradable polymeric additives may be degradable by hydrolysis to liberate the tracer functional group from the degradable polymeric additive, forming the base polymeric additive and the tracer functional compound, as previously described. The degradable polymeric additives are thermally and chemically stable for a relatively short period, which is sufficient to accomplish their goal of providing a means for tracing subterranean formations or marking wellbore cuttings, among their many uses.

In one or more embodiments, the degradable polymeric additives may fully degrade at a pH of 13.0 or greater and a temperature of 95° C. or greater in 3 days or less, such as 2 days or less, or such as 24 hours or less. In one or more embodiments, the degradable polymeric additives may fully degrade in a subterranean formation after 5 months or less, such as 2 month or less, such as 4 weeks or less, or such as 2 weeks or less, at any pH.

Drilling Fluids

One of ordinary skill in the art would appreciate that fluids of different chemical compositions may be used in drilling and production processes. For instance, during drilling operations, drilling fluids or drill-in fluids may be introduced through the drill string and egress through the bit nozzles to remove the cuttings, clean the bit, transport the cuttings to the surface, and prevent fluid loss or particulate invasion to the reservoir, among other purposes. Similarly, during fracturing or stimulation operations of low permeable formations, a fracturing or stimulation fluid may be pumped into the formation to improve the fluid flow characteristics of the field.

The term "drilling fluid" for the purposes of this application refers to fluids, slurries, or muds used in drilling operations downhole, such as during the formation of the wellbore.

In one or more embodiments, the drilling fluid may be a water-based drilling fluid or mud (WBM). In one or more embodiments, the drilling fluid may be oil-based drilling fluid or mud (OBM).

The base fluid for a drilling fluid of one or more embodiments may comprise water. Water-based materials comprise at least 50 weight percent of an WBM; a minor part may include hydrocarbons of some sort (an emulsion). Water may comprise one or more known compositions of water, including distilled; condensed; filtered or unfiltered fresh surface or subterranean waters, such as water sourced from lakes, rivers or aquifers; mineral waters; gray, brown, black, and blue waters; run-off, storm or waste water; potable or non-potable waters; brackish waters; synthetic or natural sea waters; synthetic or natural brines; formation waters; production water; boiler feed water; condensate water; and combinations thereof. The water may include impurities, including, but not limited to, ions, salts, minerals, polymers, organic chemicals, inorganic chemicals, detritus, flotsam, debris, and dead and living biological life forms, so long as the purpose and performance of the drilling fluid is not mitigated or otherwise detrimentally affected.

The base fluid for the drilling fluid of one or more embodiment may comprise a petroleum or fraction thereof. Petroleum-based materials comprise at least 50 weight percent of an OBM. Examples of suitable base petroleum materials include crude oils, distilled fractions of crude oil, including, but not limited to, heavy naphtha, diesel, kerosene, mineral oil (aromatic and dearomatized), and heavy petroleum refinery liquid residues. A minor part of the OBM is typically water or an aqueous solution that resides internally in the continuous petroleum phase (that is, an invert emulsion). Other OBM components can include emulsifiers, wetting agents, and other additives that give desirable physical properties.

Oil-based muds also include synthetic oil-based muds (SOBMs). Synthetic oil-based muds are crude oil derivatives that have been chemically treated, altered or and refined to enhance certain chemical or physical properties. In comparison to a crude temperature fraction of a partially-refined crude oil, which may contain several classes (for example, alkane, aromatic, sulfur-bearing, nitrogen-bearing) of thousands of individual compounds, a SOBM can comprise one class with only tens of individual compounds (for example, esters compounds in a $C_{8-14}$ range). Examples of materials used as base fluids for SOBMs include linear alpha olefins, isomerized olefins, poly alpha olefins, linear alkyl benzenes, and vegetable and hydrocarbon-derived ester compounds. SOBMs are monolithic systems that behave in a manner as if they were an oil-based mud but provide a more narrow and predictable range of chemical and physical behaviors.

The drilling fluid of one or more embodiments may comprise a degradable polymeric additive in a range of from about 0.00001 to 5 wt. % (weight percent) of the drilling fluid. For example, the drilling fluid may contain the degradable polymeric additives that is of an amount ranging from a lower limit of any one of 0.00001, 0.0001, 0.001, 0.01, 0.1, 1.0, and 2.0 wt. % to an upper limit of any one of 0.1, 0.5, 1.0, 2.0, 3.0, and 5.0 wt. %, where any lower limit can be used in combination with any mathematically-compatible upper limit.

The drilling fluid of one or more embodiments may have a pH of greater than about 6.5. For example, the drilling fluid may have a pH that is of an amount ranging from a lower limit of any one of 6.5, 7.0, 7.5, 8.0, 9.0, and 10.0 to an upper limit of any one of 7.0, 7.5, 8.5, 9.5, 11.0, and 13.0, where any lower limit can be used in combination with any mathematically-compatible upper limit. The drilling fluid composition may be maintained in a specific pH range, for example, an alkaline pH range, by adding a pH buffer, such as sodium hydroxide.

In one or more embodiments, the drilling fluid may have a density that is equal to or greater than about 1.00 $g/cm^3$. For example, the drilling fluid may have a density that is of an amount ranging from a lower limit of any of 1.00, 1.10, 1.20, 1.30, 1.50, 1.80, and 2.0 $g/cm^3$ to an upper limit of any of 1.40, 1.60, 1.80, 2.00, 2.20, 2.50, and 3.00 $g/cm^3$, where any lower limit can be used in combination with any mathematically-compatible upper limit.

The drilling fluid of one or more embodiments may contain additional polymeric additives to modify other drilling fluid properties, such as viscosity control, scale inhibition, and biodegradation prevention. Other examples of polymeric additives may include, but are not limited to, polyacrylamides, polyacrylic acids, polysaccharides, polyamines, and surfactants that are commonly used in drilling muds.

In one or more embodiments, the typical funnel viscosity of the drilling fluid is in the range of from about 40 to 150 seconds. For example, the drilling fluid may have a funnel viscosity in a range having a lower limit of any of 40, 45, 50, 60, 70, and 80 seconds to an upper limit of any of 80, 90, 100, 110, 120, 130, 140, and 150 seconds, where any lower limit can be used in combination with any mathematically-compatible upper limit.

In one or more embodiments, a degradable polymeric additive may be incorporated into an aqueous or oil-based fluid, such as, but not limited to, a drilling fluid, a stimulation fluid, a fracturing fluid, a spotting fluid, a clean-up fluid, a completion fluid, a remedial treatment fluid, an abandonment fluid, a pill, an acidizing fluid, a cementing fluid, a packer fluid, or a combination thereof. In one or more embodiments, a drilling fluid may comprise a degradable polymeric additive.

Methods of Use

Figure 2:
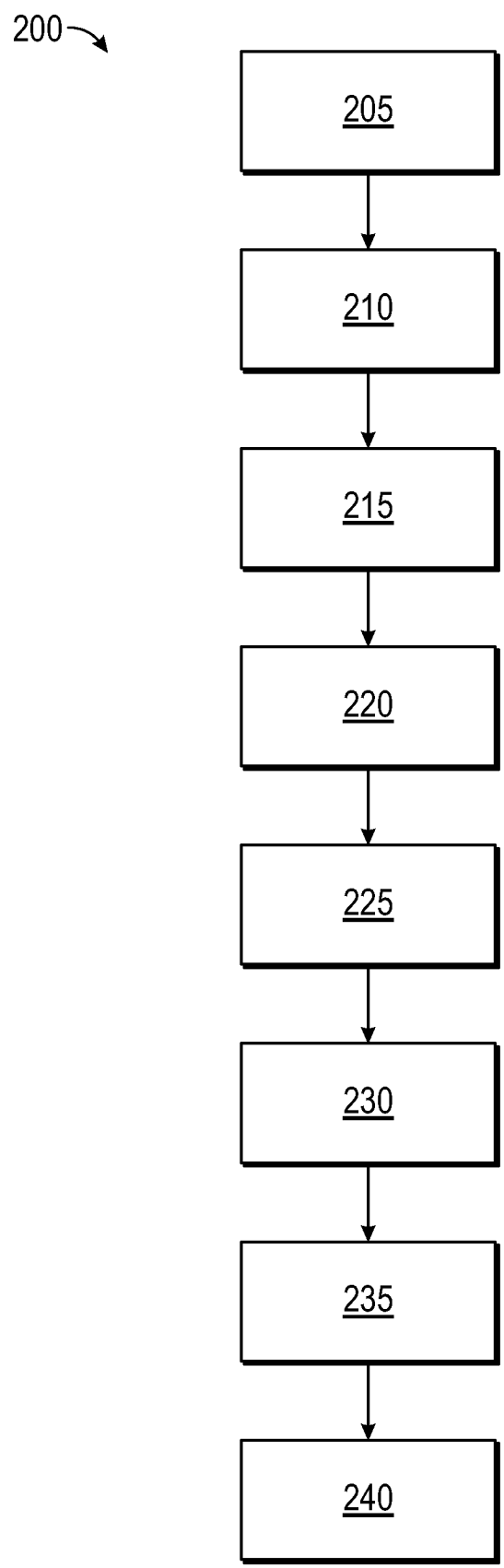
FIG. 2 depicts a method of use of the degradable polymeric additives in accordance with one or more embodiments.

FIG. 2 depicts a method of use of the degradable polymeric additives in accordance with one or more embodiments. In one or more embodiments, method 200 continues in that a degradable polymeric additive is created by reaction between a base polymeric component and a tracer functional compound 205. Such reactions are demonstrated in FIG. 1A-C as well as described in the several EXAMPLES.

The method 200 includes introducing an amount of the degradable polymeric additive into a drilling fluid to form an altered drilling fluid 210. In one or more embodiments, the base fluid for the drilling fluid comprises water, petroleum, or a petroleum fraction. An amount of degradable polymeric additive to introduce into the drilling fluid is described previously.

The method 200 continues with the introducing the altered drilling fluid into a wellbore 215. The altered drilling fluid traverses downhole and contacts a wellbore cutting proximate to the drill bit. Upon contact with the wellbore cutting, the degradable polymer additive leaves the drilling fluid and associates with the wellbore cutting. The altered drilling fluid converts into a depleted drilling fluid.

The wellbore cutting is formed at a given depth of the drill bit. The depth of the drill bit is known at the time of association. The degradable polymer additive associates with the wellbore cutting through several potential means, such as through impregnation or reaction. The wellbore cuttings convert into associated wellbore cuttings.

The method 200 includes detecting the presence of degradable polymer additive in the depleted drilling fluid 220. The associated wellbore cuttings and the depleted drilling fluid are conveyed uphole to the surface via the wellbore annulus as part of the circulation of the drilling fluid through the wellbore. The drilling fluid is depleted of degradable polymer additive; however, in some instances it may not free of the degradable polymer additive. In some instances, not all the degradable polymer additive has associated with the associated wellbore cuttings; some is still present in the depleted drilling fluid returning to the surface.

The method 200 includes recovering the associated wellbore cutting from the depleted drilling fluid 225. The associated wellbore cuttings may be recovered through any normal sampling means of collecting wellbore cutting samples at the surface, which is known to those of skill in the art.

The method 200 continues with treating of the depleted drilling fluid to degrade any remaining degradable polymer additive 230. Upon degrading the degradable polymer additive in the depleted drilling fluid, the drilling fluid re-forms and is ready for return to the mud cycle. Upon degrading the degradable polymer additive in the depleted drilling fluid, the drilling fluid re-forms and is ready for return to the mud cycle.

The method 200 includes pre-treating the associated wellbore cuttings to remove depleted drilling fluid and preparing for analysis 235. The pre-treatment of the associated wellbore cuttings prevents the detection of previously degraded degradable polymer additive that is present in the depleted wellbore fluid. Even at the brief time exposure downhole, it is expected that a small amount of the degradable polymer additive will degrade back into its base polymeric component and a tracer functional compound. Pre-treatment avoids any false positive results from detecting the tracer functional compound.

The method 200 continues with detecting the presence of degradable polymeric additives associated with wellbore cuttings 240. The wellbore cuttings 240 recovered from the field may be subjected to a Py GC-MS analysis after pre-cleaning step 235. Pyrolysis, at the temperatures greater than the thermal degradation of breaking the hydrolysable covalent bond, will thermally release the tracer functional group from the base polymeric component, allowing the tracer functional group to be detected by the Py GC-MS spectrometer. The pyrolysis of one or more embodiments may be performed at a temperature in a range of from about 300 to 600° C. For example, the pyrolysis may be performed at a temperature ranging from a lower limit of any one of 300, 350, 400, 450, 500, and 550° C. to an upper limit of any one of 400, 450, 500, 550, and 600° C., where any lower limit can be used in combination with any mathematically-compatible upper limit.

EXAMPLES

The following examples are merely illustrative and should not be interpreted as limiting the scope of the present disclosure.

General Materials and Methods (FT-IR, TGA, GC-MS):

All chemicals were purchased from VWR and used as received. $^1H$ and $^{13}C$ NMR spectra were obtained on a Bruker Advance III 500 MHz spectrometer in DMSO-$d_6$ or $D_2O$ at room temperature with 16 scans and 10,000 scans, respectively. Chemical shifts are reported relative to the solvent peaks. FT-IR spectra were acquired on a Nicolet iS50R instrument with 64 scans at 4 $cm^{-1}$ (1/centimeters) resolution.

TGA Measurements

Thermogravimetric analysis (TGA) of the polymers was performed on a TA Instruments Discovery TGA, scanning from 25-600° C. at a scan rate of 20° C./min under $N_2$.

Pyrolysis GC-MS Measurements

Py GC-MS was performed on a Frontier model PY-30305 pyrolizer linked to an Agilent 7000D QQQ system. The degradable polymeric additives were pyrolyzed at 550° C. for 0.4 min (minute). The column used for separation was an Agilent HP-5 ms UI (ultra-inert) column with the following specifications: 30 m (meter) length, 0.25 mm (millimeters) inner diameter (ID), and 0.25 μm (nanometer) film. The set temperature of the back inlet was 280° C. with split ratio of 50:1 and split flow of 25 mL/min (milliliters/minute). The flow rate of the carrier He gas through the column was 0.5 mL/min at a constant flow mode. The column/oven temperature started at 45° C. and increased to 300° C. at 10° C./min (degrees Celsius/minute).

Synthesis of Starch 4-Chlorobenzoate (SCB)

Figure 3A:
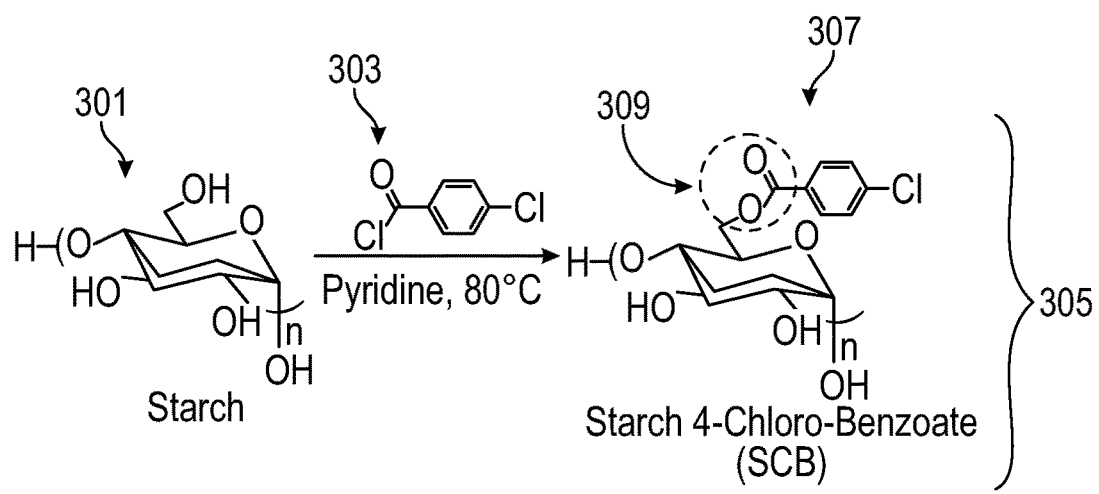
FIG. 3A is a schematic illustration depicting the preparation of starch 4-chlorobenzoate (SCB), which is a degradable polymeric additive, according to one or more of the embodiments.

FIG. 3A is a schematic illustration depicting the preparation of starch 4-chlorobenzoate (SCB), which is a degradable polymeric additive, according to one or more of the embodiments. FIG. 3A shown starch 301, 4-chlorobenzoate 303, starch 4-chlorobenzoate (SCB) 305, tracer functional groups 307, and hydrolysable covalent bond 309.

In a 50 mL round bottom flask, 0.5 grams (g) of starch (3.1 mmol (millimoles) repeating unit (polysaccharide term anhydrous glucose unit (AGU)) and 20 mL (milliliters) of pyridine were added. The heterogeneous mixture was stirred for 12 h (hours) at room temperature. Subsequently, 4-chlorobenzoyl chloride (1.98 mL, 5 equivalents (eq) per repeating unit) was added dropwise to the solution at room temperature followed by addition of 4-dimethylaminopyridine (20 mg) (milligrams). The reaction mixture was stirred at 80° C. for 24 h and a homogeneous solution was obtained. The solution was then precipitated in ethanol (200 mL) followed by filtration to recover the precipitate. The isolated crude product was re-dissolved in DMSO (10 mL) and re-precipitated in ethanol, before vacuum drying at room temperature to yield starch 4-chlorobenzoate (SCB). Yield: 0.9032 g.

Figure 4A:
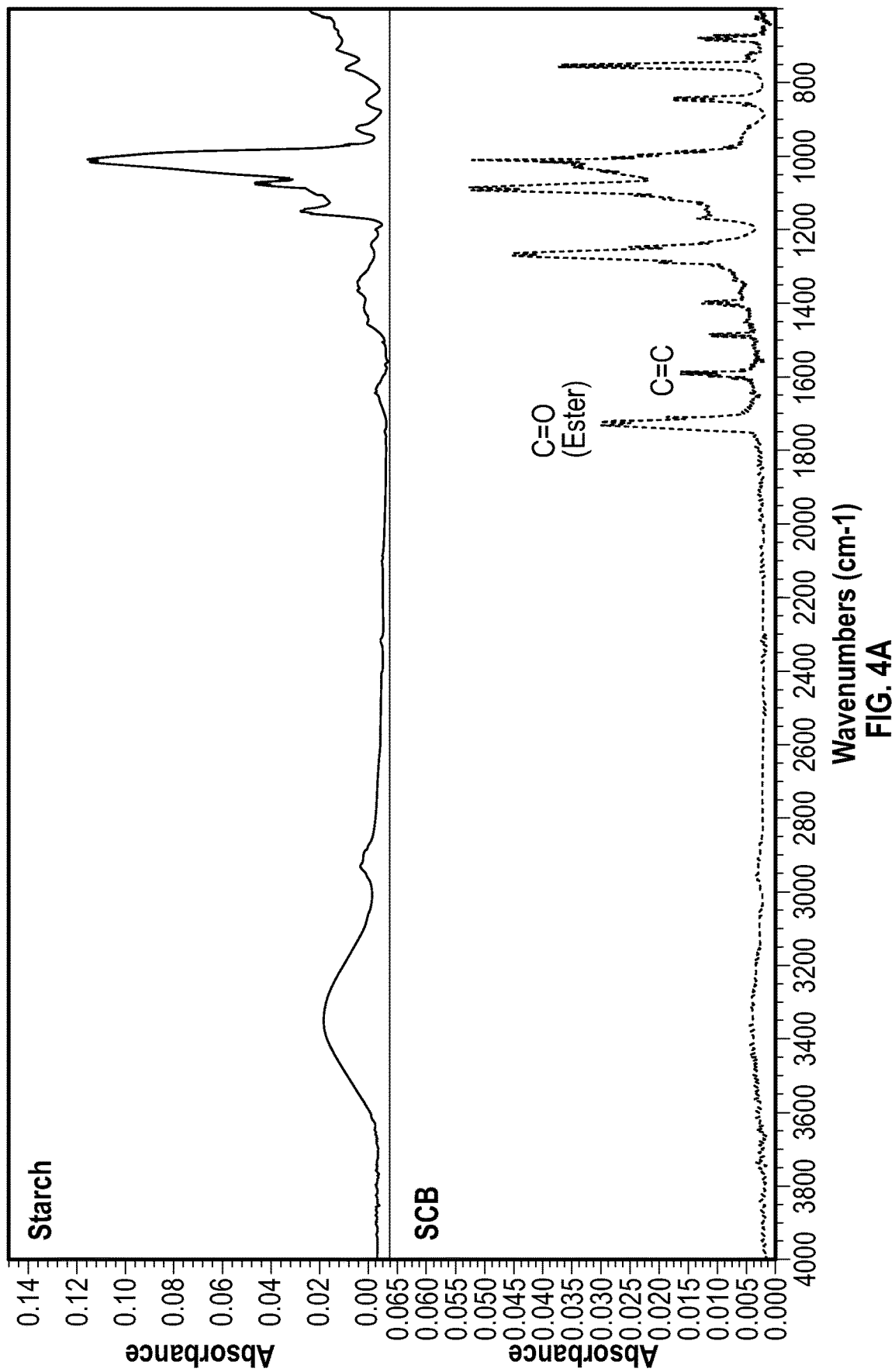
FIG. 4A depicts the FT-IR spectra of polysaccharide term anhydrous glucose unit (AGU) and SCB, which is a degradable polymeric additive, respectively, according to one or more embodiments.

FIG. 4A depicts the FT-IR spectra of polysaccharide term anhydrous glucose unit (AGU) and SCB, respectively, according to one or more embodiments. The structure of SCB was confirmed by FT-IR and $^1H$ NMR spectroscopy. The FT-IR spectrum displayed a strong ester carbonyl (C═O) absorption around 1750 $cm^{-1}$ (1/centimeters) and a carbon-carbon double bond (C═C) stretch at 1600 $cm^{-1}$ confirming successful esterification of starch.

Figure 4B:
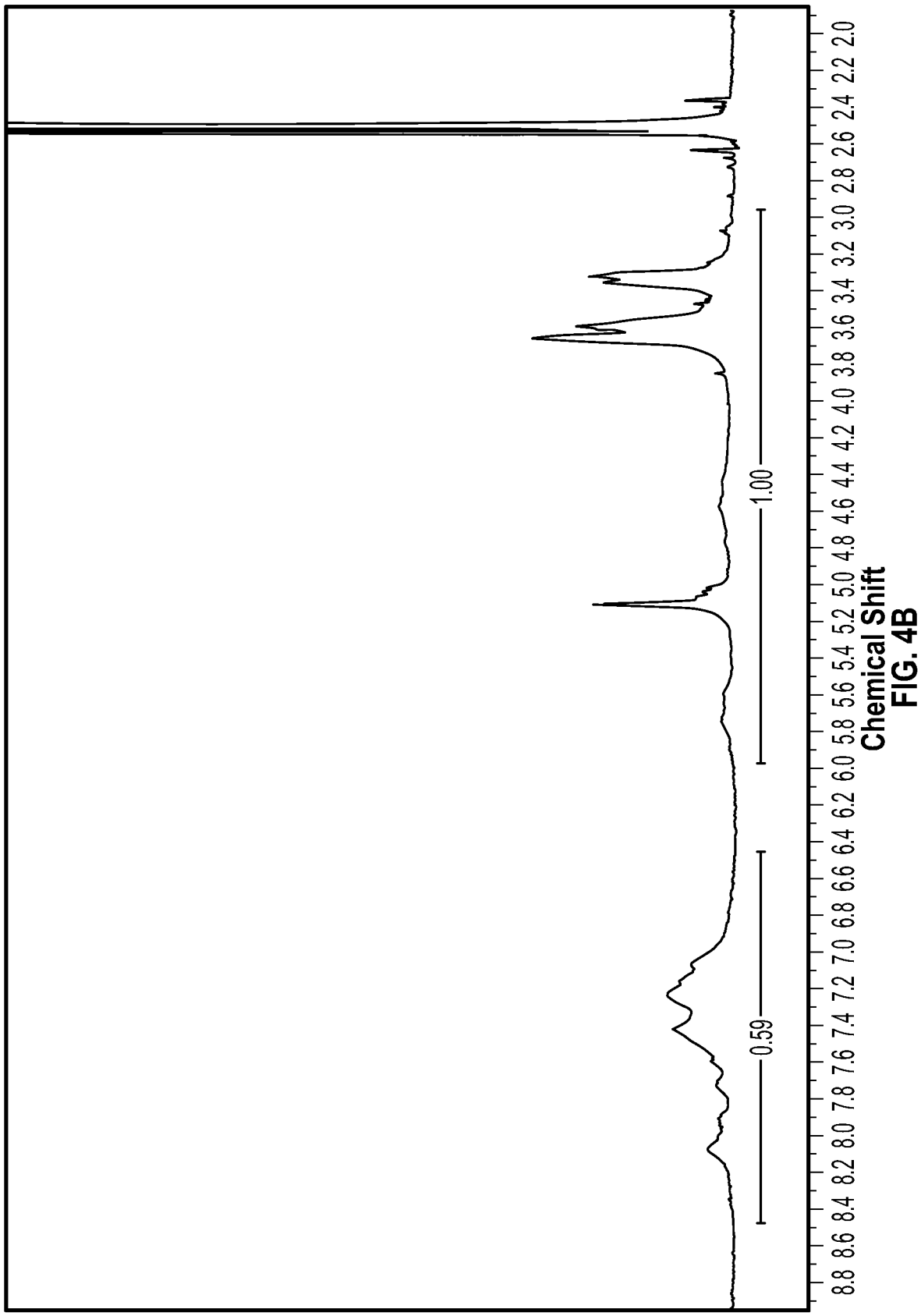
FIG. 4B depicts the $^1$H NMR of SCB, which is a degradable polymeric additive according to one or more embodiments.

FIG. 4B depicts the $^1H$ NMR spectra of SCB, which is a degradable polymeric additive, according to one or more embodiments. In the $^1H$ NMR spectrum, the product showed new peaks in the range of from about 6.82-8.35 ppm (parts per million), which correlate to the aromatic protons. The broad aromatic proton peaks and lack of sharp peaks in the $^1H$ NMR spectrum indicate the successful linkage of the aromatic rings to the polymer backbone and confirm the absence of a small molecule impurity. SCB is found to be soluble only in hot DMSO; this limited solubility creates a challenge in acquiring a $^{13}$C NMR spectrum with a high signal to noise ratio. $^1$H NMR (500 MHz, DMSO-d$_6$): 3.09-5.96 (starch backbone) and 6.82-8.35 (aromatic protons).

Figure 4C:
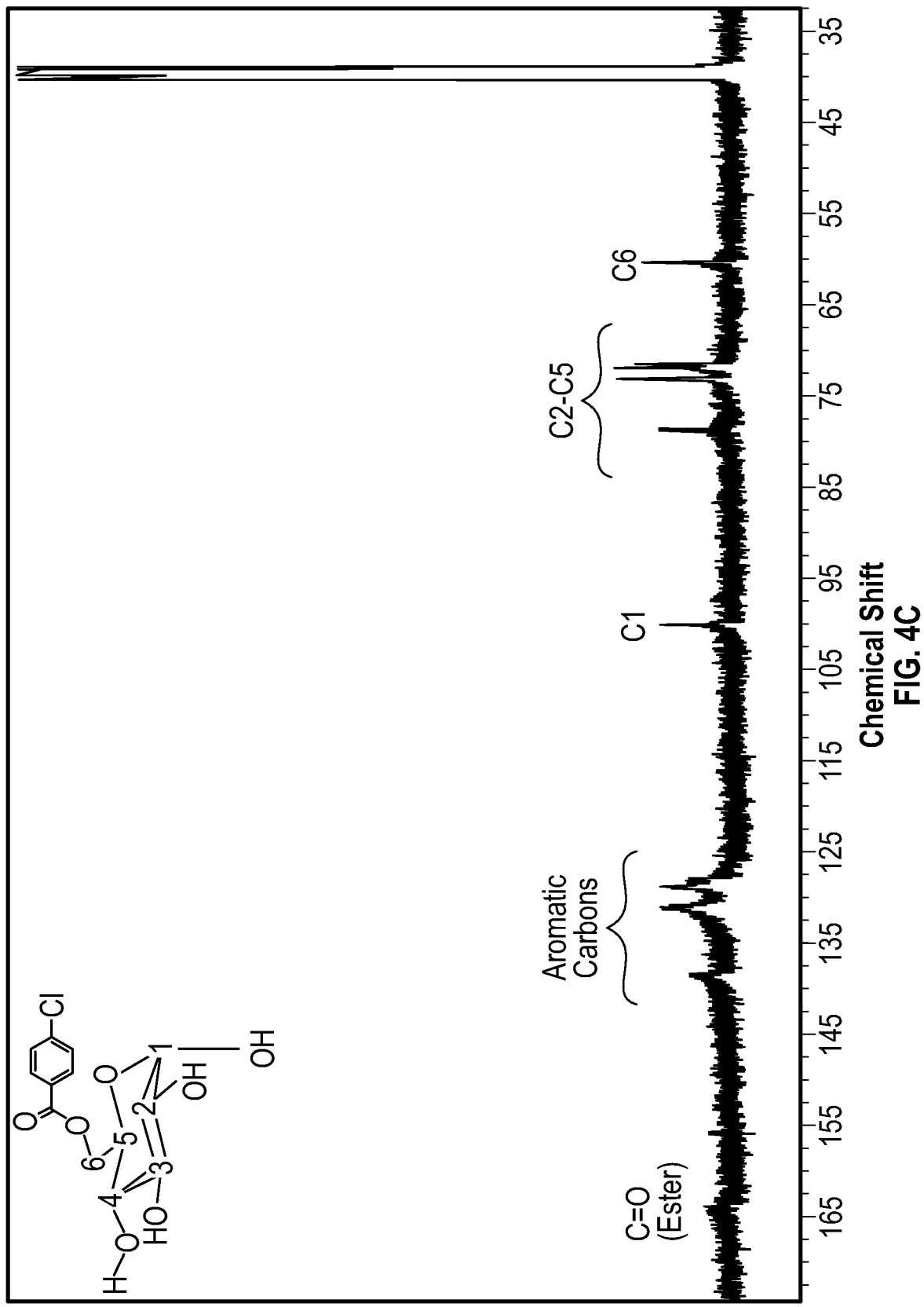
FIG. 4C depicts $^{13}$C NMR spectra of SCB, which is a degradable polymeric additive according to one or more embodiments.

FIG. 4C depicts $^{13}$C NMR spectra of SCB, which is a degradable polymeric additive, according to one or more embodiments. New peaks in the $^{13}$C NMR spectrum are detectable at 128.85, 131.36, 138.63 ppm, which arise from the aromatic carbons, and at 164.44 ppm (O—(C=O)—) (peak is not as clear as others), correlating to the ester carbonyl. $^{13}$C NMR (500 MHz, DMSO-d$_6$): δ0.46 (C6), 71.58, 71.95, 73.24, 78.74 (C2-C5), 100.08 (C1), 128.85, 131.36, 138.63 (aromatic ring), 164.44 (O—(C=O)—).

Synthesis of Xanthan 4-Chlorobenzoate (XCB)

Figure 3B:
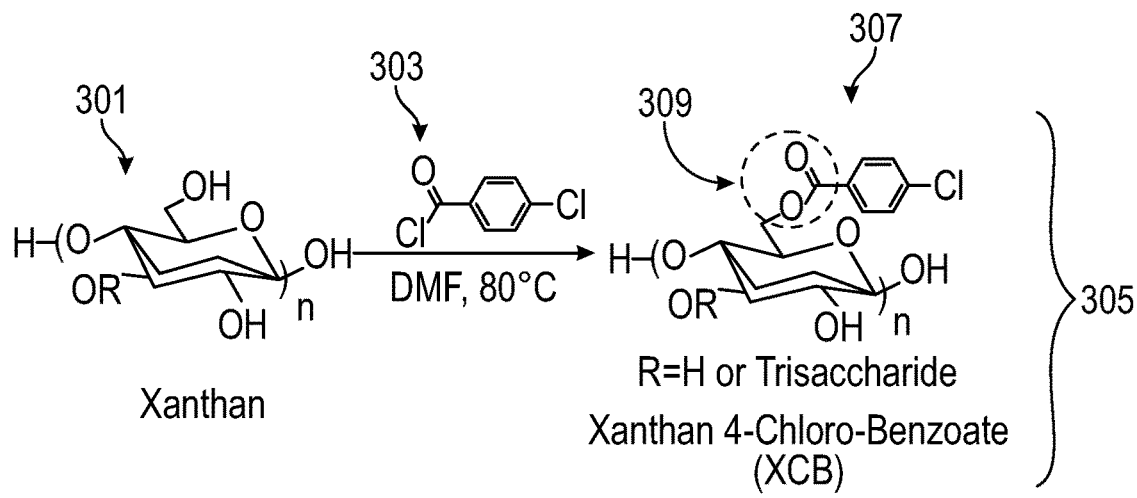
FIG. 3B is a schematic illustration depicting the preparation of starch 4-chlorobenzoate (XCB), which is a degradable polymeric additive, according to one or more of the embodiments.

FIG. 3B is a schematic illustration depicting the preparation of starch 4-chlorobenzoate (XCB), which is a degradable polymeric additive, according to one or more of the embodiments. FIG. 3B shown xanthan gum 301, 4-chlorobenzoate 303, xanthan 4-chlorobenzoate (XCB) 305, tracer functional groups 307, and hydrolysable covalent bond 309.

0.5 grams of xanthan gum (3.1 mmol repeating unit (polysaccharide term anhydrous glucose unit AGU)) and 15 mL of DMF were mixed in a 100 mL round bottom flask. The heterogeneous mixture was stirred for 12 h at room temperature. Subsequently, 4-chlorobenzoyl chloride (1.98 mL, 5 eq per repeating unit) and pyridine (2.44 mL, 5 eq per repeating unit) were added dropwise to the solution at room temperature, followed by addition of 4-dimethylaminopyridine (20 mg). The reaction mixture was stirred at 80° C. for 24 h and a homogeneous solution was obtained. The product was then precipitated out in acetone (200 mL), followed by filtrating and extensive washing with ethanol before vacuum drying at room temperature to yield xanthan 4-chlorobenzoate (XCB). Yield: 0.5030 g.

Figure 5:
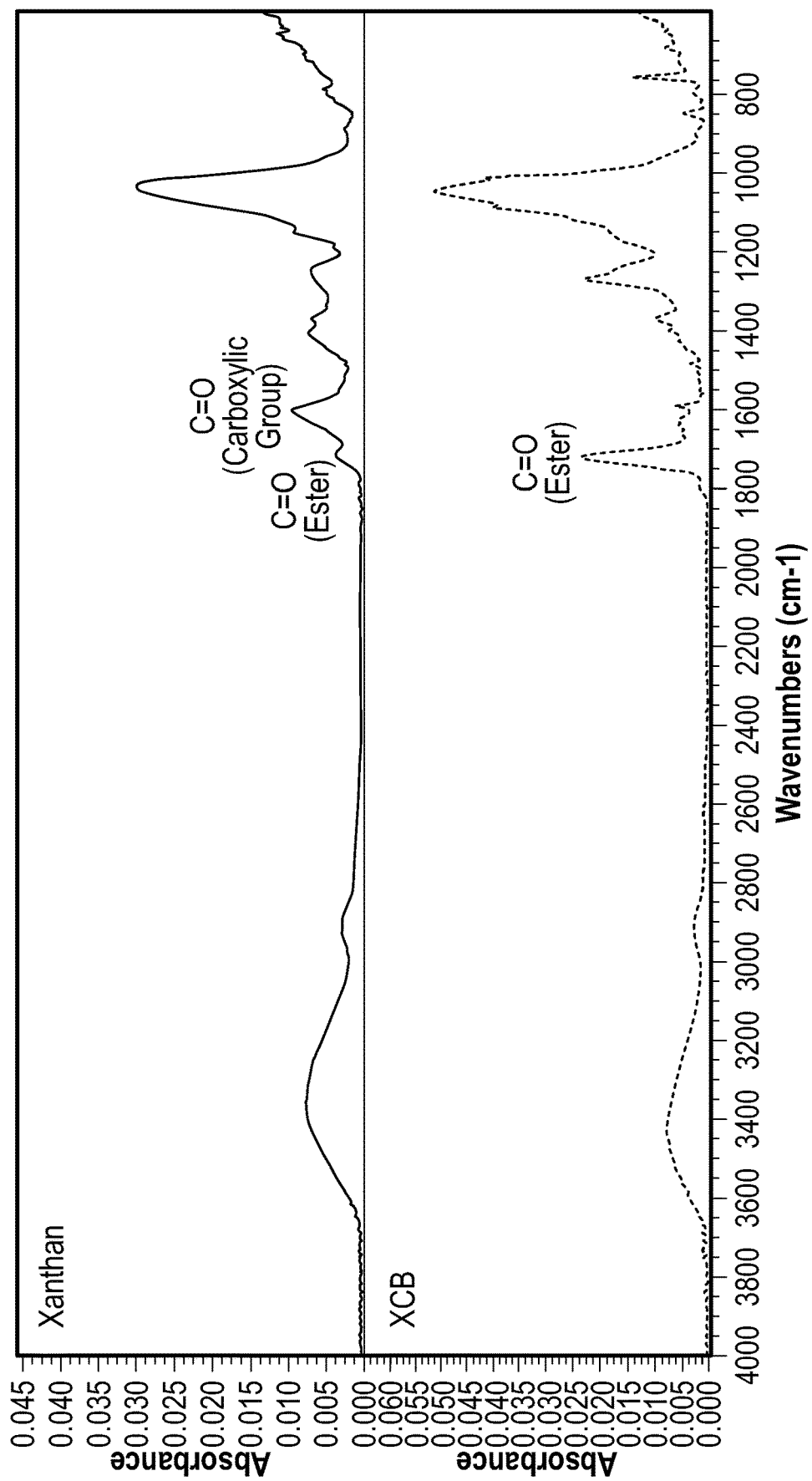
FIG. 5 depicts the FT-IR spectra of xanthan gum and XCB, which is a degradable polymeric additive, respectively, according to one or more embodiments.

FIG. 5 depicts the FT-IR spectra of xanthan gum and XCB, a degradable polymeric additive, respectively, according to one or more embodiments. The esterification of xanthan gum was confirmed by FT-IR by the strong increase in the ester carbonyl signal at 1750 cm$^{-1}$. The esterified xanthan was found to be insoluble in common organic solvents and aqueous fluids; therefore, NMR spectra is unavailable.

Synthesis of Starch 4-Fluorobenzoate (SFB)

Figure 3C:
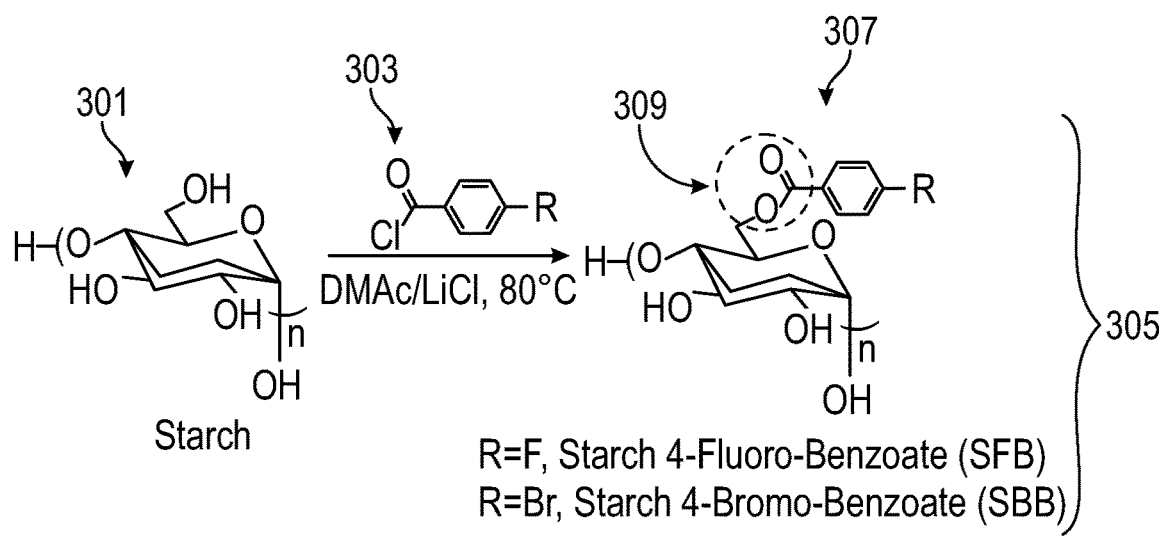
FIG. 3C is a schematic illustration depicting the preparation of starch 4-fluorobenzoate (SFB) and starch 4-bromobenzoate (SBB), both of which are degradable polymeric additives, according to one or more of the embodiments.

FIG. 3C is a schematic illustration depicting the preparation of starch 4-fluorobenzoate (SFB), which is a degradable polymeric additive, according to one or more of the embodiments. FIG. 3C shown starch 301, 4-fluorobenzoate 303, starch 4-fluorobenzoate (SFB) 305, tracer functional groups 307, and hydrolysable covalent bond 309.

Starch (1.000 grams, 6.2 mmol repeating unit (polysaccharide term anhydrous glucose unit (AGU))) was dissolved in DMAc (40 mL)/LiCl (2.000) grams as previously provided. 4-flurobenzoyl chloride (3.65 mL, 5 eq per repeating unit) and pyridine (2.44 mL, 5 eq per repeating unit) were then added to the starch solution in DMAc/LiCl. The solution was heated at 80° C. for 24 h. Next, the solution was poured into 200 mL of ethanol, followed by filtration of the precipitate. The crude product was re-dissolved in DMAc (5 mL) and re-precipitated in ethanol (100 mL) twice, then washed extensively with water. The product was dried in vacuo at room temperature overnight to afford starch 4-flurobenzoate (SFB). Yield: 1.9768 g.

Figure 6B:
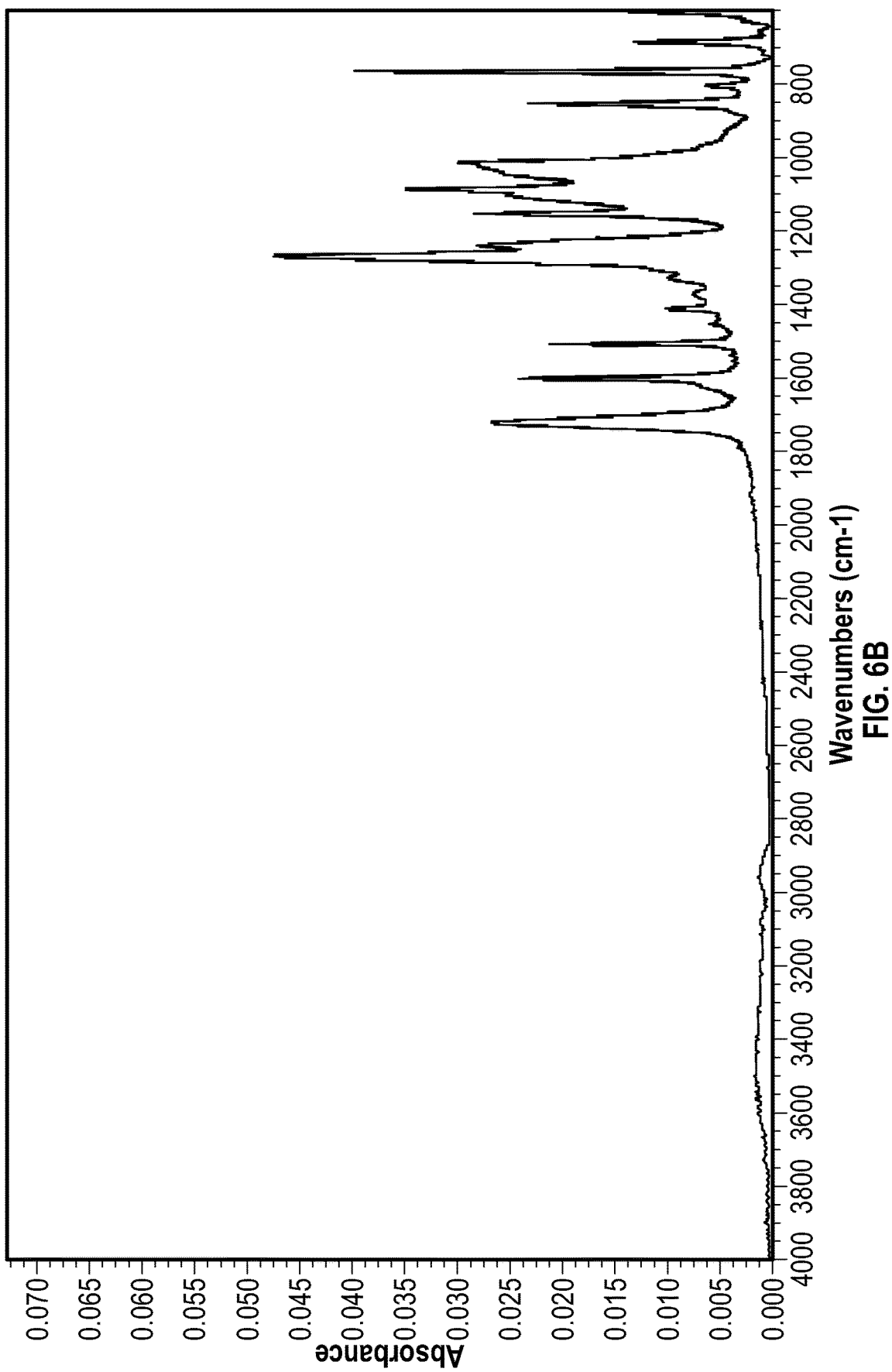
FIG. 6B depicts the FT-IR spectra of starch 4-fluorobenzoate (SFB), a degradable polymeric additive, which is according to one or more embodiments.

FIG. 6A depicts the $^1$H NMR spectra of starch 4-fluorobenzoate (SFB), which is a degradable polymeric additive, according to one or more embodiments. $^1$H NMR (FIG. 6) (500 MHz, DMSO-d$_6$): 3.13-5.85 (starch backbone) and 7.13-8.43 (aromatic protons). FIG. 6B depicts the FT-IR spectra of starch 4-fluorobenzoate (SFB), a degradable polymeric additive, according to one or more embodiments. The structures of SFB was confirmed by the broad aromatic signal from 6.5 to 8.5 ppm in $^1$H NMR spectra, the ester carbonyl absorption at 1750 cm$^{-1}$ in the FT-IR spectrum, and carbon-carbon double bond absorption at 1600 cm$^{-1}$ in the FT-IR spectra. The $^1$H NMR spectra indicate the presence of residual solvents, DMAc, and ethanol in the polymers, which need further purification. We observed that the acquired SFB under the DMAc/LiCl system have significantly enhanced solubility in organic solvents. SFB is soluble in DMSO, acetone, and THF (there might be small particles or floating particles, but the majority of the polymers are soluble).

Synthesis of Starch 4-Bromobenzoate (SBB)

FIG. 3C is also a schematic illustration depicting the preparation of starch 4-bromobenzoate (SBB), which is a degradable polymeric additive, according to one or more of the embodiments. FIG. 3C shown starch 301, 4-bromobenzoate 303, starch 4-bromobenzoate (SBB) 305, tracer functional groups 307, and hydrolysable covalent bond 309.

Starch (0.500 grams, 3.1 mmol repeating unit (polysaccharide term anhydrous glucose unit AGU)) and N,N-dimethylacetamide (20 mL) was stirred in a 50 mL round bottom flask. The reaction mixture was heated to 120° C. and stirred for 30 minutes, followed by addition of anhydrous LiCl (1.000 grams). The mixture was slowly cooled to room temperature and a homogeneous mixture was obtained after stirring for 1 hour. The mixture was then stirred overnight.

4-bromobenzoyl chloride (3.387 g, 5 eq. per repeating unit) was slowly added to the solution and the solution was heated at 80° C. for 24 h. The solution was precipitated into 200 mL of ethanol and the crude product was collected by filtration. The crude product was re-dissolved in DMAc (5 mL), re-precipitated in ethanol (100 mL) twice, and washed extensively with water. The product was dried in vacuo at room temperature overnight to afford starch 4-bromobenzoate (SBB). Yield: 0.9832 g.

Figure 7A:
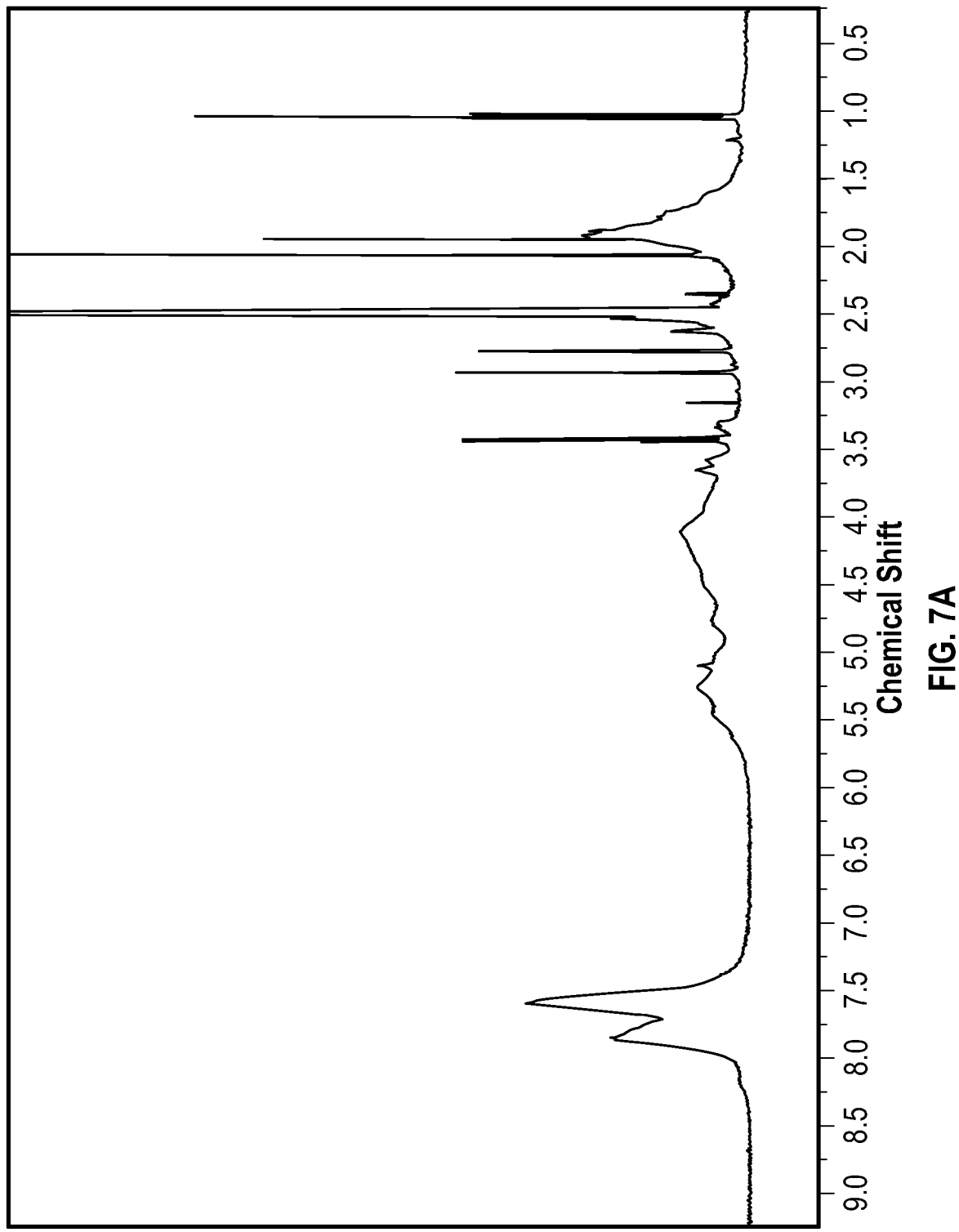
FIG. 7A depicts the $^1$H NMR spectra of starch 4-bromobenzoate (SBB), a degradable polymeric additive, which is according to one or more embodiments.
Figure 7B:
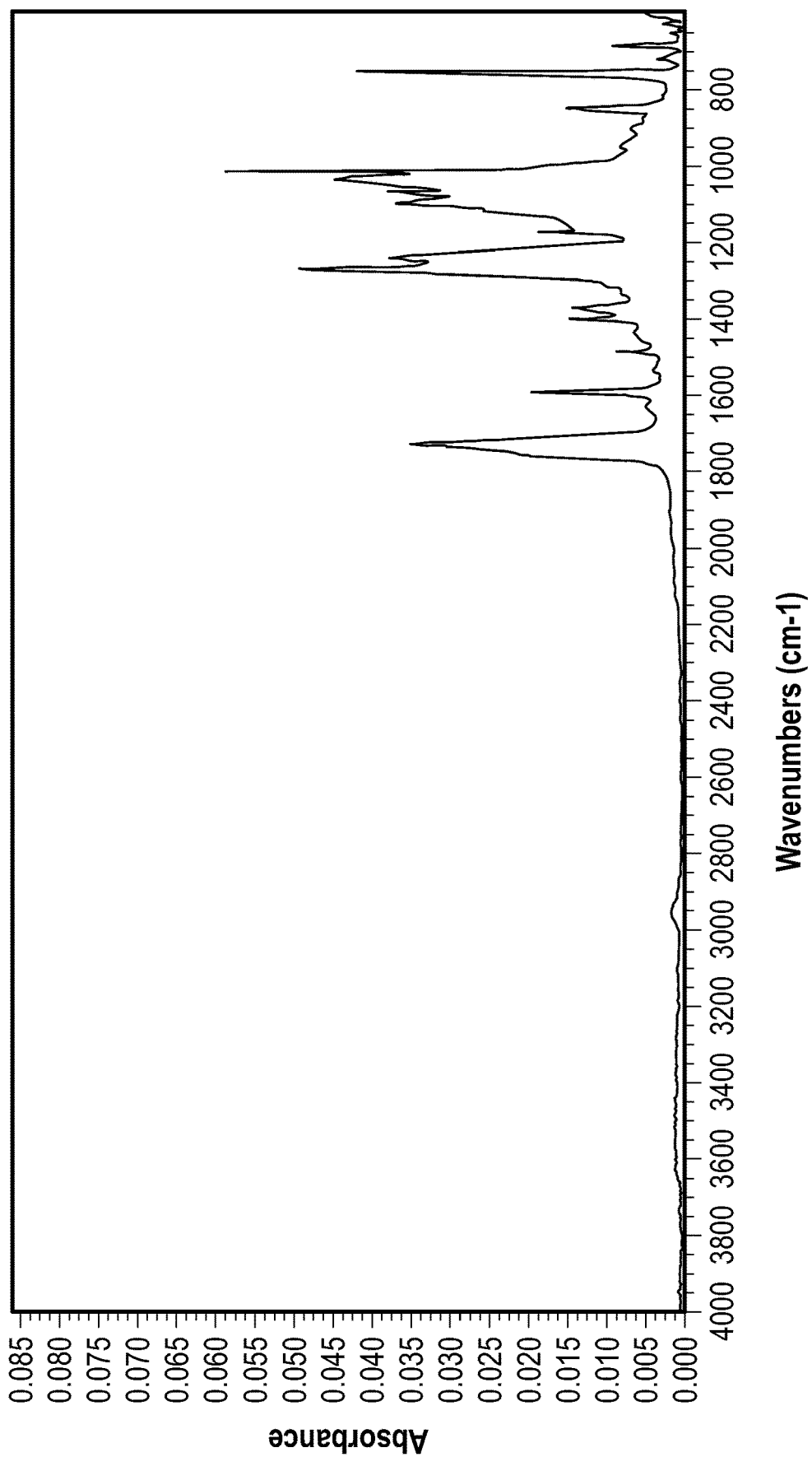
FIG. 7B depicts the FT-IR spectra of starch 4-bromobenzoate (SBB), a degradable polymeric additive, which is according to one or more embodiments.

FIG. 7A depicts the $^1$H NMR spectra of starch 4-bromobenzoate (SBB), which is a degradable polymeric additive, according to one or more embodiments. $^1$H NMR (500 MHz, DMSO-d$_6$): 3.13-5.85 (starch backbone) and 7.13-8.43 (aromatic protons). FIG. 7B depicts the FT-IR spectra of starch 4-bromobenzoate (SBB), which is a degradable polymeric additive, according to one or more embodiments. The structures and solubility of SBB is similar to that observed for SFB, described previously.

Synthesis of Dextran 4-Bromobenzoate (DBB)

Figure 3D:
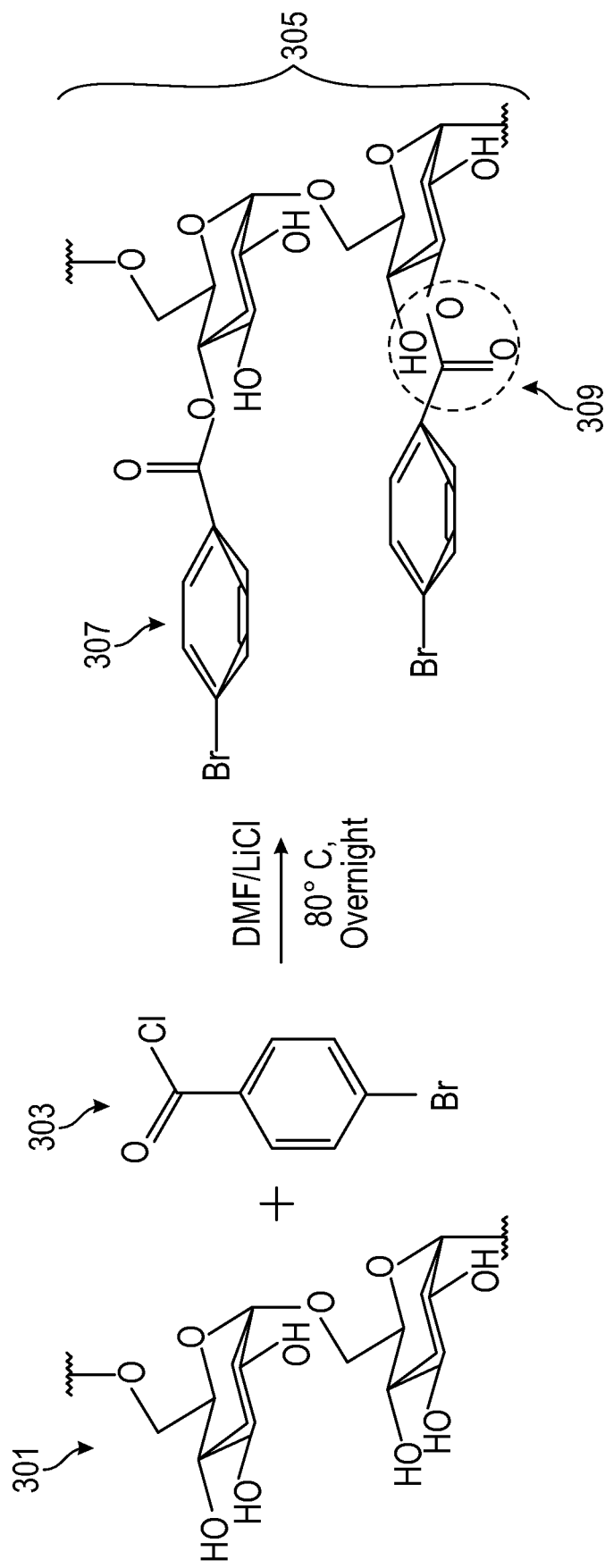
FIG. 3D is also a schematic illustration depicting the preparation of dextran 4-bromobenzoate (DBB), which is a degradable polymeric additive, according to one or more of the embodiments.

FIG. 3D is a schematic illustration depicting the preparation of dextran 4-bromobenzoate (DBB), which is a degradable polymeric additive, according to one or more of the embodiments. FIG. 3D shown dextran 301, 4-bromobenzoate 303, dextran 4-bromobenzoate (DBB), tracer functional groups 307, and hydrolysable covalent bond 309.

The synthesis of dextran-4-bromobenzoate (DBB) commenced with degassing DMF/LiCl solution (20 mL/0.5 g) with N$_2$ and heating the solution to 90° C. Dextran (0.4 g, 150 k M$_W$ from L. mesenteroides) was dissolved in the solution and the temperature was decreased to 80° C. Pyridine (0.9717 g, 12.3 mmol) and 4-bromobenzoyl chloride (2.7 g, 12.3 mmol) were added to the mixture. The reaction was allowed to proceed overnight. The product was precipitated with cold isopropyl alcohol, filtered, and washed with isopropyl alcohol (IPA) (15 mL×2) to yield a light-yellow viscous product. The viscous product was redissolved via sonication in DMF at 50° C. and reprecipitated with IPA to yield an off-white solid.

Figure 17A:
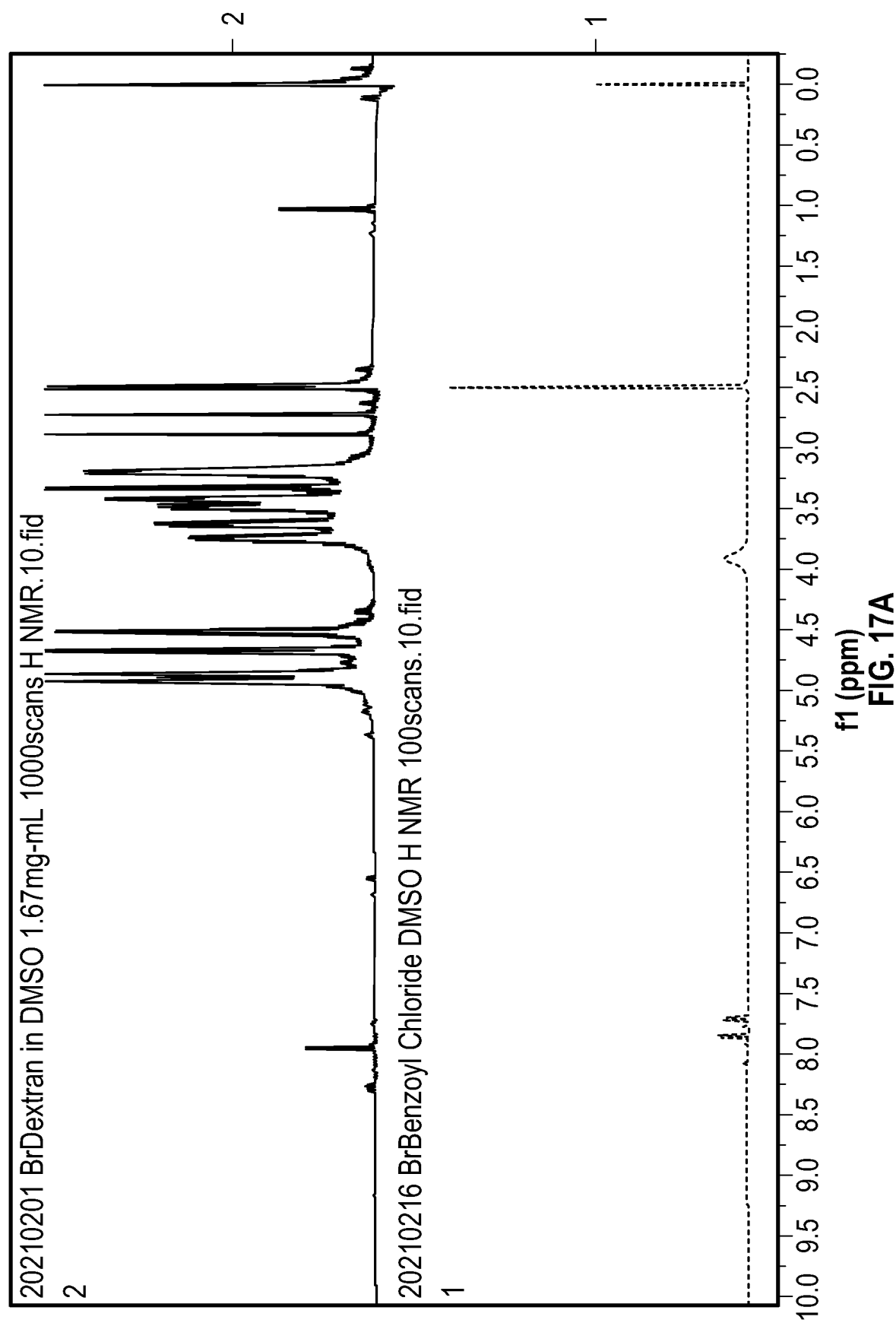
FIG. 17A depicts $^1$H NMR spectra of dextran-4-bromobenzoate (DBB), which is a degradable polymeric additive, according to one or more embodiments, and 4-bromobenzoyl chloride.

FIG. 17A depicts $^1$H NMR spectra of dextran-4-bromobenzoate (DBB), which is a degradable polymeric additive, according to one or more embodiments, and 4-bromobenzoyl chloride. The $^1$H NMR shows peaks in the aromatic region corresponding to the linked bromobenzene on the dextran (DBB). The peaks shift relative to the aromatic peaks of free bromobenzyol chloride. Note that the spectrum contains a tetramethylsilane (TMS) internal standard peak at 0 ppm, solvent residual peak at 2.50 ppm, trace water at 3.34 ppm, and dimethylformamide (DMF) peaks at 2.73, 2.89, and 7.95 ppm. $^1$H NMR 4-bromobenzoyl chloride (500 MHz, DMSO-d$_6$) δ 13.14 (s, 2H), 8.09-8.04 (m, 1H), 7.99-7.89 (m, 1H), 7.86 (d, J=8.4 Hz, 5H), 7.79 (dd, J=16.9, 8.4 Hz, 1H), 7.71 (d, J=8.4 Hz, 4H). $^1$H NMR dextran-4-bromobenzoate (500 MHz, DMSO-d$_6$) δ 4.92 (d, J=5.2 Hz, 2H), 4.86 (d, J=4.4 Hz, 2H), 4.69-4.65 (m, 2H), 4.51 (d, J=5.9 Hz, 2H), 3.75 (d, J=9.3 Hz, 2H), 3.66-3.60 (m, 2H), 3.52-3.38 (m, 4H), 3.25-3.14 (m, 4H).

Figure 17B:
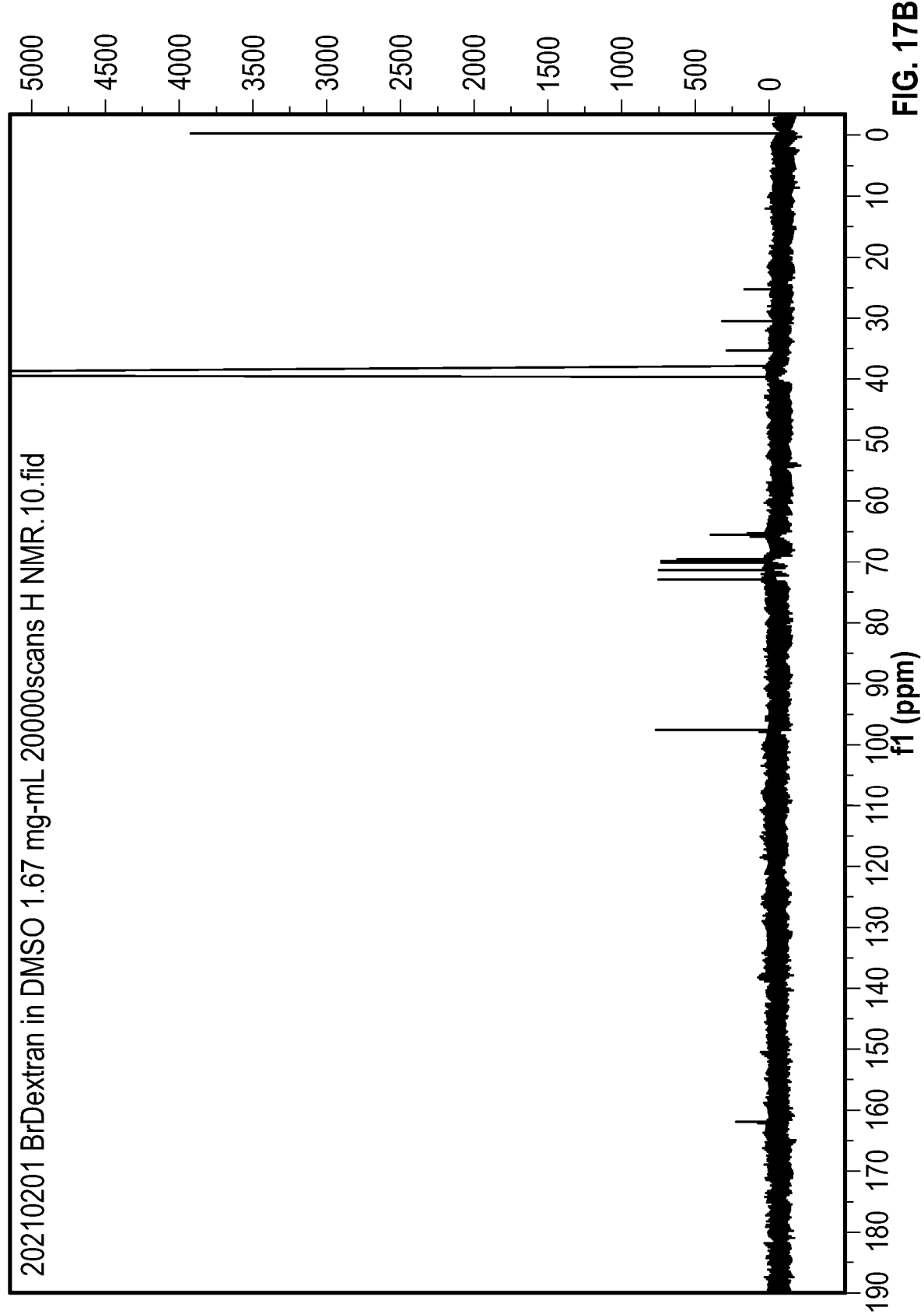
FIG. 17B depicts $^{13}$C NMR spectra of DBB, which is a degradable polymeric additive, according to one or more embodiments.

FIG. 17B depicts $^{13}$C NMR spectra of DBB, which is a degradable polymeric additive, according to one or more embodiments. The $^{13}$C NMR confirms the formation of an ester bond, as illustrated by the downfield carbon carbonyl peak at 162.34. $^{13}$C NMR dextran-4-bromobenzoate (500 MHz, DMSO-d$_6$) δ 162.34, 98.24, 73.33, 71.85, 70.39, 70.12, 66.08, 35.81, 30.79, 25.52.

Overall, we have synthesized SCB and XCB heterogeneously in pyridine or DMF, and SBB and SFB homogeneously in DMAc/LiCl.

TGA Measurements

Thermogravimetric analysis (TGA) of the polymers was performed on a TA Instruments Discovery TGA, scanning from 25 to 600° C. at a scan rate of 20° C./min.

Figure 8A:
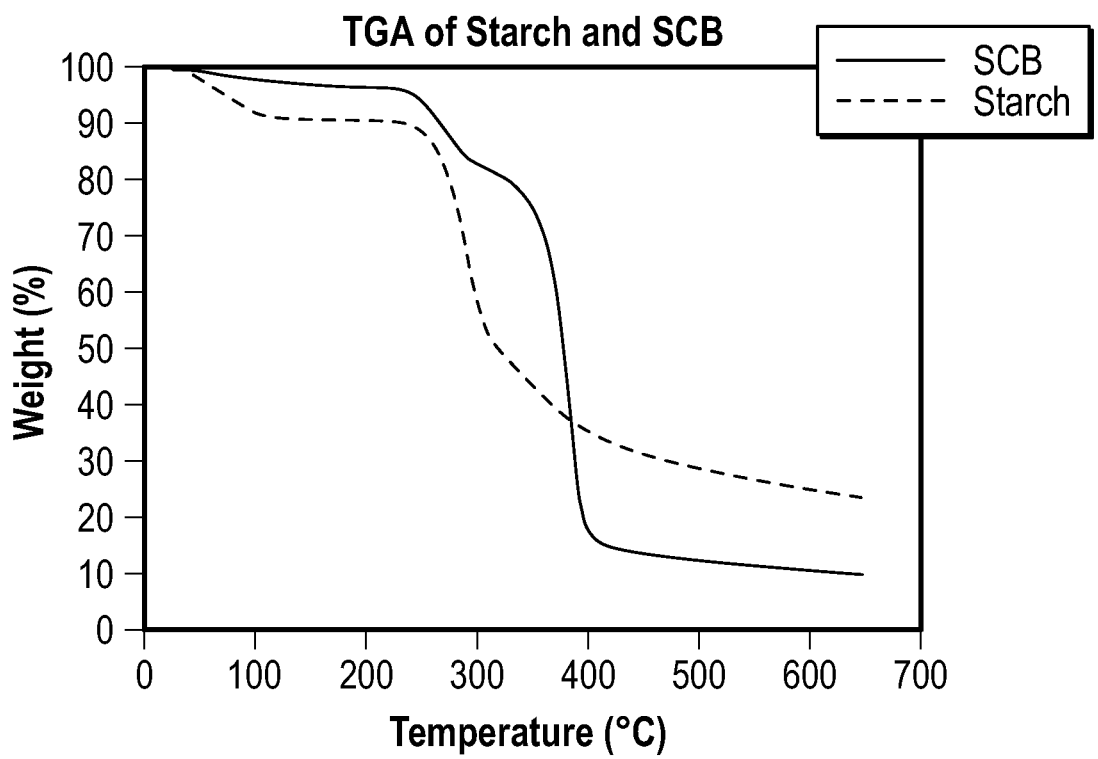
FIG. 8A depicts the thermogravimetric analyses of starch and starch 4-chlorobenzoate (SCB), which is a degradable polymeric additive, according to one or more embodiments.

FIG. 8A depicts the thermogravimetric analyses of starch and starch 4-chlorobenzoate (SCB), which is a degradable polymeric additive, according to one or more embodiments.

Figure 8B:
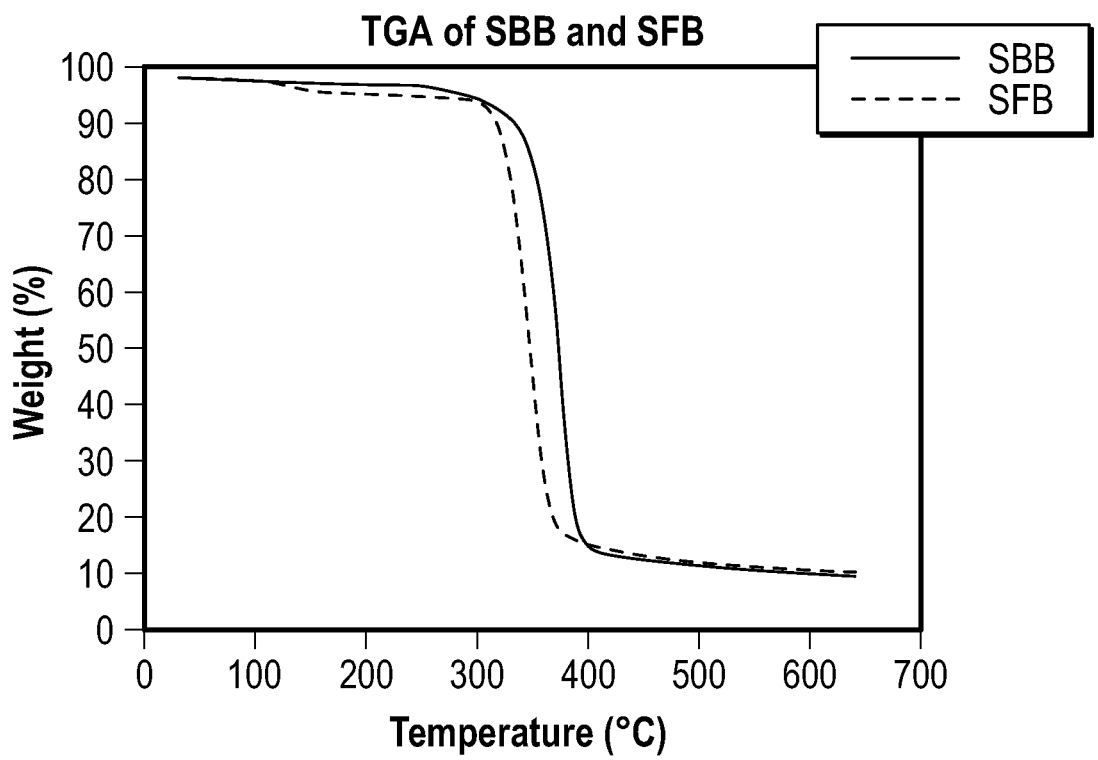
FIG. 8B depicts the thermogravimetric analyses of starch and starch 4-bromobenzoate (SBB), which is a degradable polymeric additive, according to one or more embodiments.

FIG. 8B depicts the thermogravimetric analyses of starch and starch 4-bromobenzoate (SBB), which is a degradable polymeric additive, according to one or more embodiments.

Py GC-MS Measurements

Figures 9A, 9B, 9C:
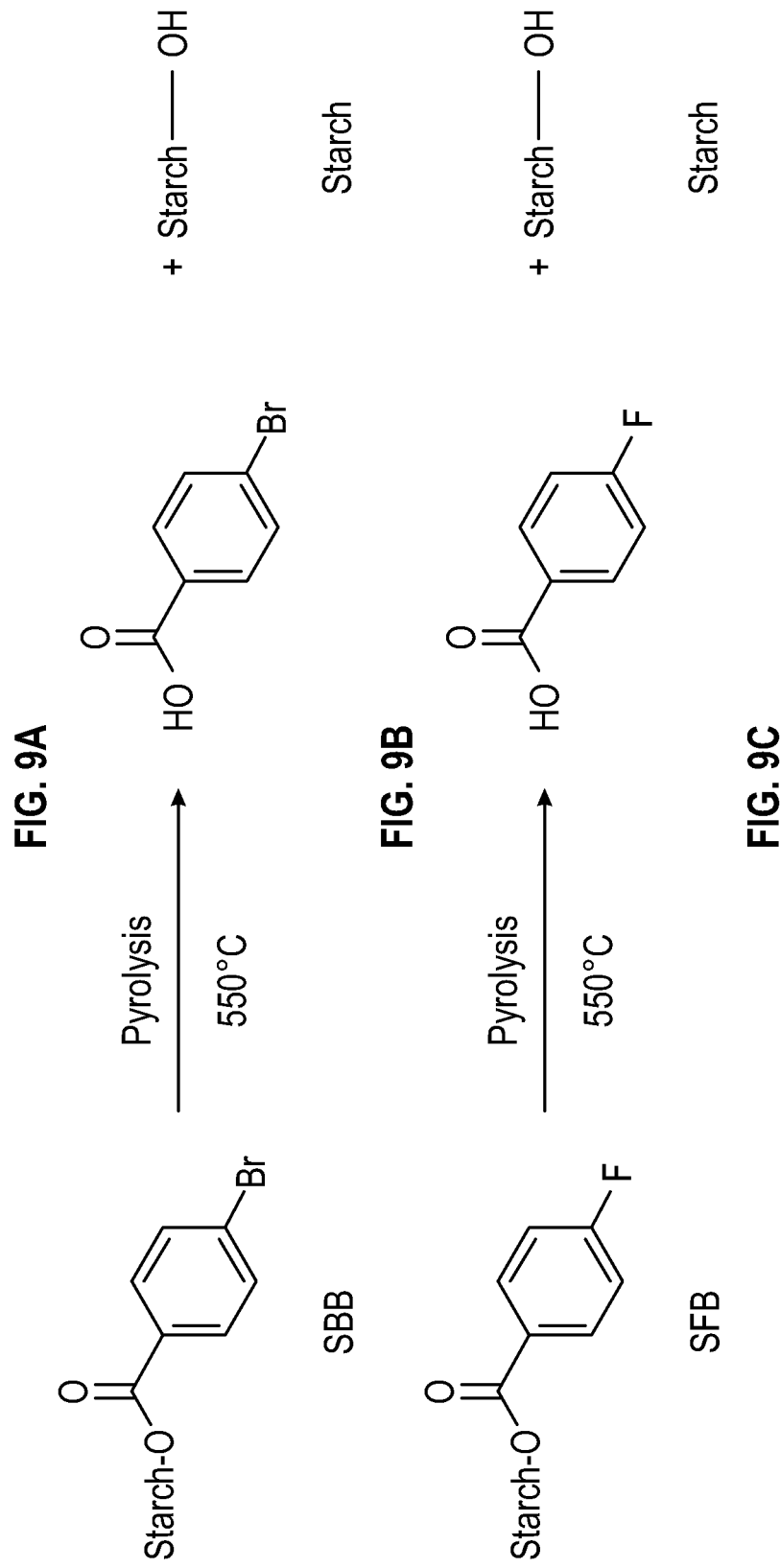
FIGS. 9A-C shows the pyrolysis degradation mechanisms of starch 4-chlorobenzoate (SCB), starch 4-bromobenzoate (SBB), and starch 4-fluorobenzoate (SFB), respectively, each of which are degradable polymeric additives, according to one or more embodiments.

FIGS. 9A-C shows the pyrolysis degradation mechanisms of starch 4-chlorobenzoate (SCB), starch 4-bromobenzoate (SBB), and starch 4-fluorobenzoate (SFB), respectively, each of which are degradable polymeric additives, according to one or more embodiments. Py GC-MS analysis confirmed the functionalization of the starch to form starch 4-chlorobenzoate (SCB), starch 4-bromobenzoate (SBB), and starch 4-fluorobenzoate (SFB).

Figure 10A:
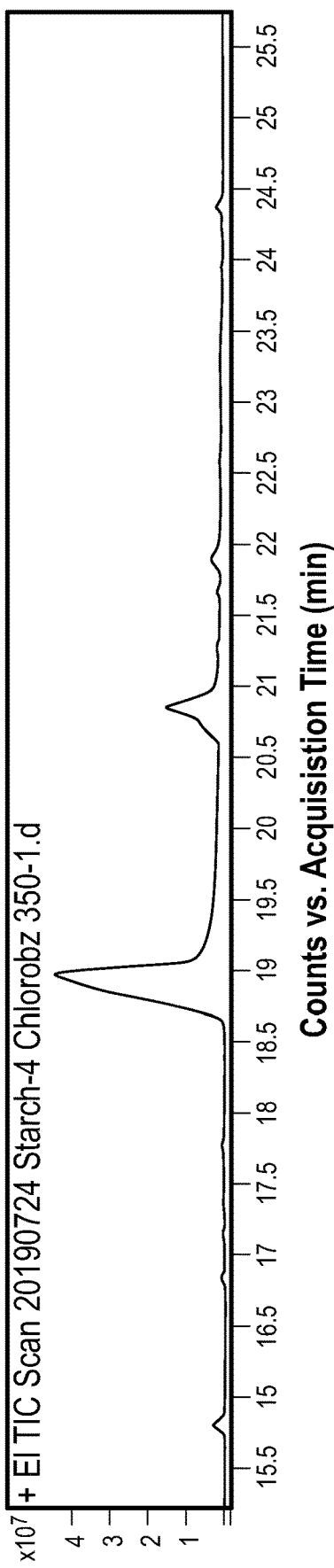
FIGS. 10A-C show the pyrolysis gas chromatography-mass spectrometry (Py GC-MS) analysis of starch 4-chlorobenzoate (SCB), which is a degradable polymeric additive, according to one or more embodiments, the Py GC-MS analysis of the degradation starch from the SCB, and the mass spectra of SCB, which is a degradable polymeric additive, according to one or more embodiments.
Figure 10B:
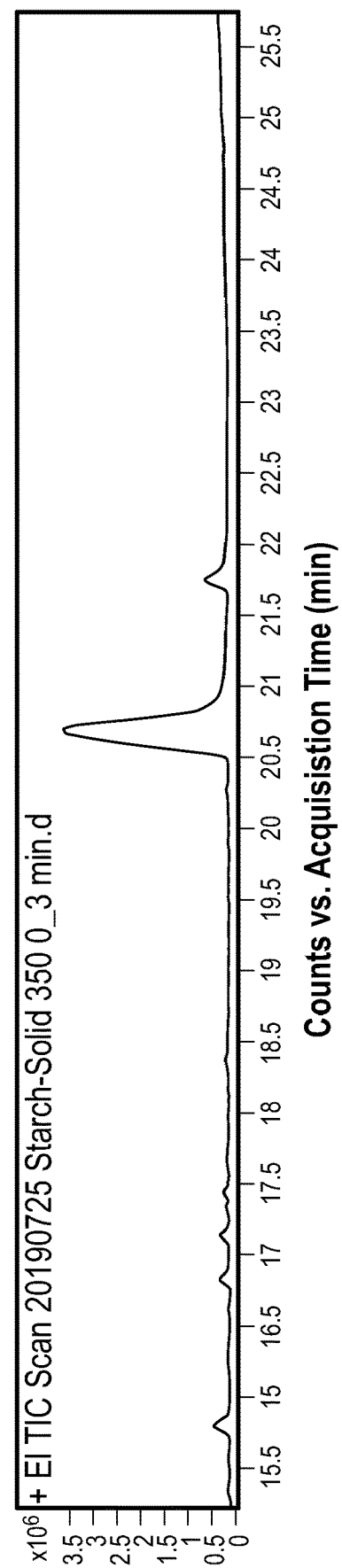
Figure 10C:
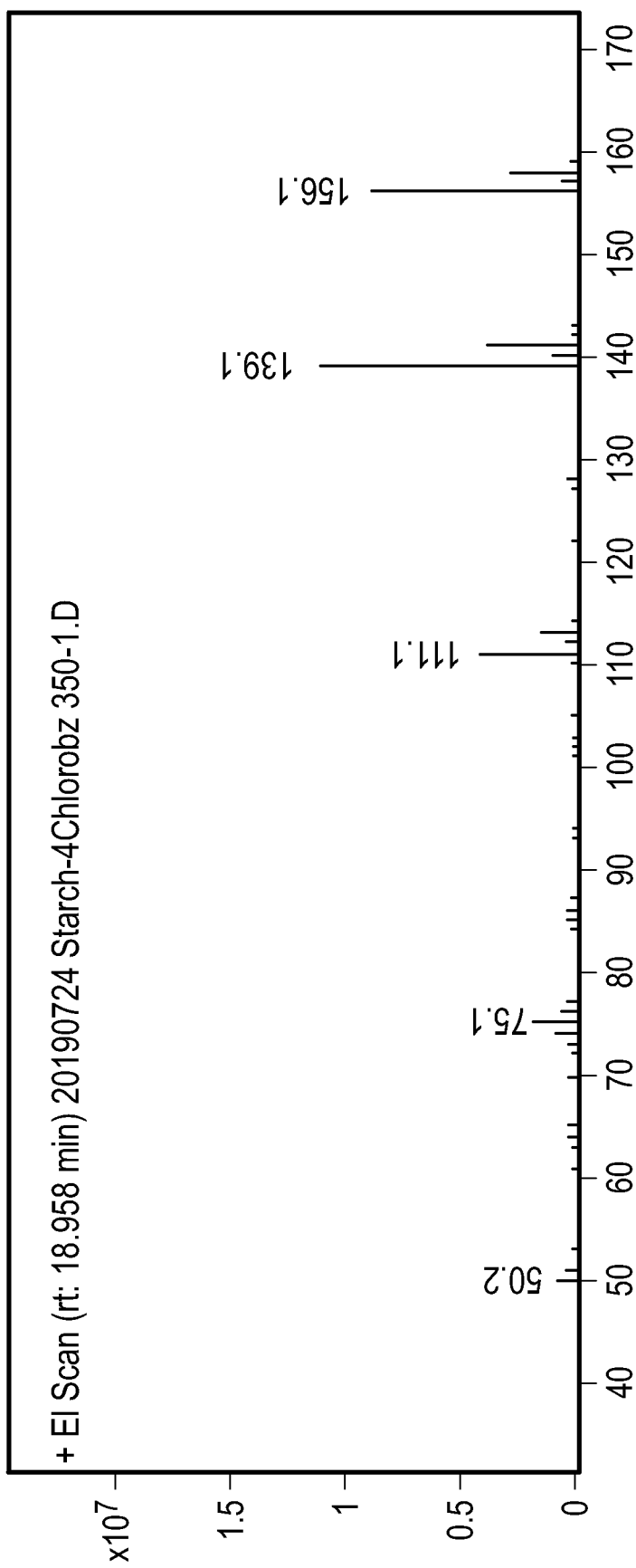

FIGS. 10A-C show the pyrolysis gas chromatography-mass spectrometry (Py GC-MS) analysis of starch 4-chlorobenzoate (SCB), which is a degradable polymeric additive, according to one or more embodiments, the Py GC-MS analysis of the starch used to form the SCB, and the mass spectra of SCB, which is a degradable polymeric additive, according to one or more embodiments. FIG. 10A depicts the (Py GC-MS) analysis of starch 4-chlorobenzoate (SCB). Chromatographic separation of SCB after pyrolysis showed the appearance of a peak at 18.958 minutes corresponding to an m/z of 156, the exact mass of 4-chlorobenzoate. FIG. 10B depicts the corresponding starch molecule used in manufacturing SCB, showing the difference in elution time from the Py GC-MS of the degradation products. FIG. 10C is the corresponding mass spectra for SCB showing the unique 3:1 isotope pattern of the M, M+2 peaks rising from the presence of the chlorine atom on the molecule.

FIGS. 11A-B show the pyrolysis gas chromatography-mass spectrometry (Py GC-MS) analysis and the mass spectra of starch 4-bromobenzoate (SBB), which is a degradable polymeric additive, according to one or more embodiments. FIG. 11A depicts the Py GC-MS analysis of SBB. FIG. 11B is the corresponding mass spectra for SBB. Chromatographic separation of SBB after pyrolysis confirmed the appearance of a peak at 20.71 minutes corresponding to an m/z of 200—the exact mass of 4-bromobenzoate, the tracer functional compound. The mass spectrometer also showed the unique 1:1 isotope pattern of the M, M+2 peaks rising from the presence of the bromine atom on the molecule.

Figure 12A:
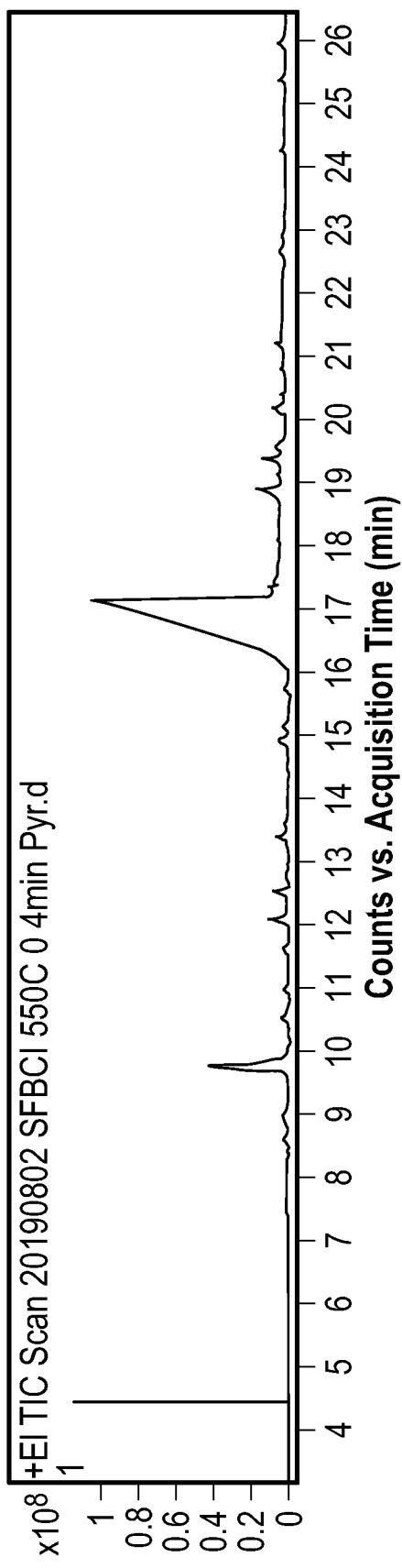
FIGS. 12A-B show the pyrolysis gas chromatography-mass spectrometry (Py GC-MS) analysis and the mass spectra of starch 4-fluorobenzoate (SFB), which is a degradable polymeric additive, according to one or more embodiments.
Figure 12B:
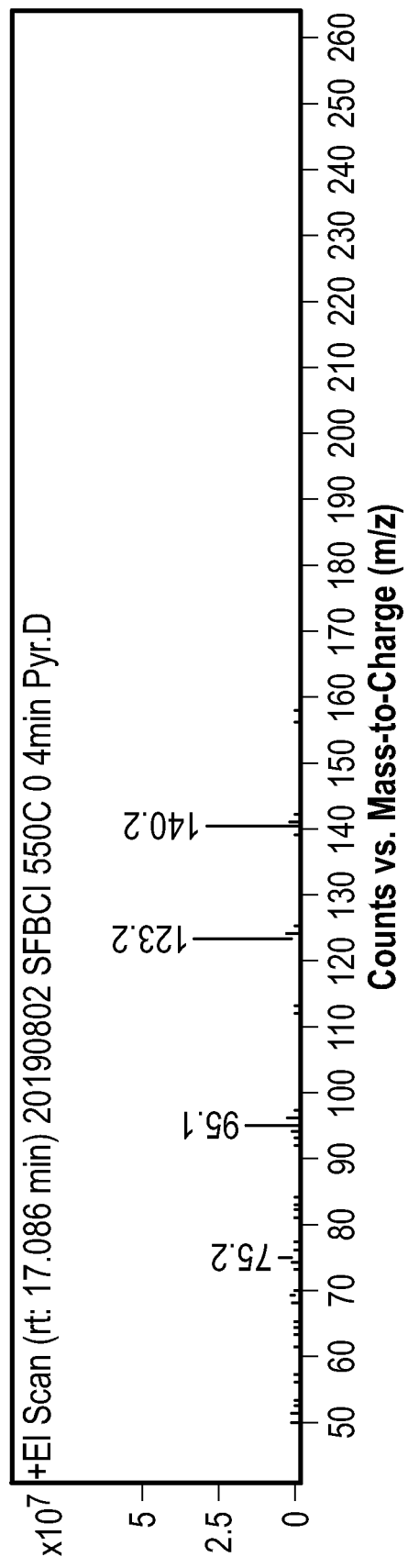

FIGS. 12A-B show the pyrolysis gas chromatography-mass spectrometry (Py GC-MS) analysis and the mass spectra of starch 4-fluorobenzoate (SFB), which is a degradable polymeric additive, according to one or more embodiments. FIG. 12A depicts the Py GC-MS analysis of SFB. FIG. 12B is the corresponding mass spectra for SFB. Py GC-MS confirmed the formation of starch 4-fluorobenzoate with the appearance of a peak at 17.086 minutes corresponding to a m/z=140, which is the exact mass of 5-fluorobenzoate, the tracer functional compound.

Figure 13A:
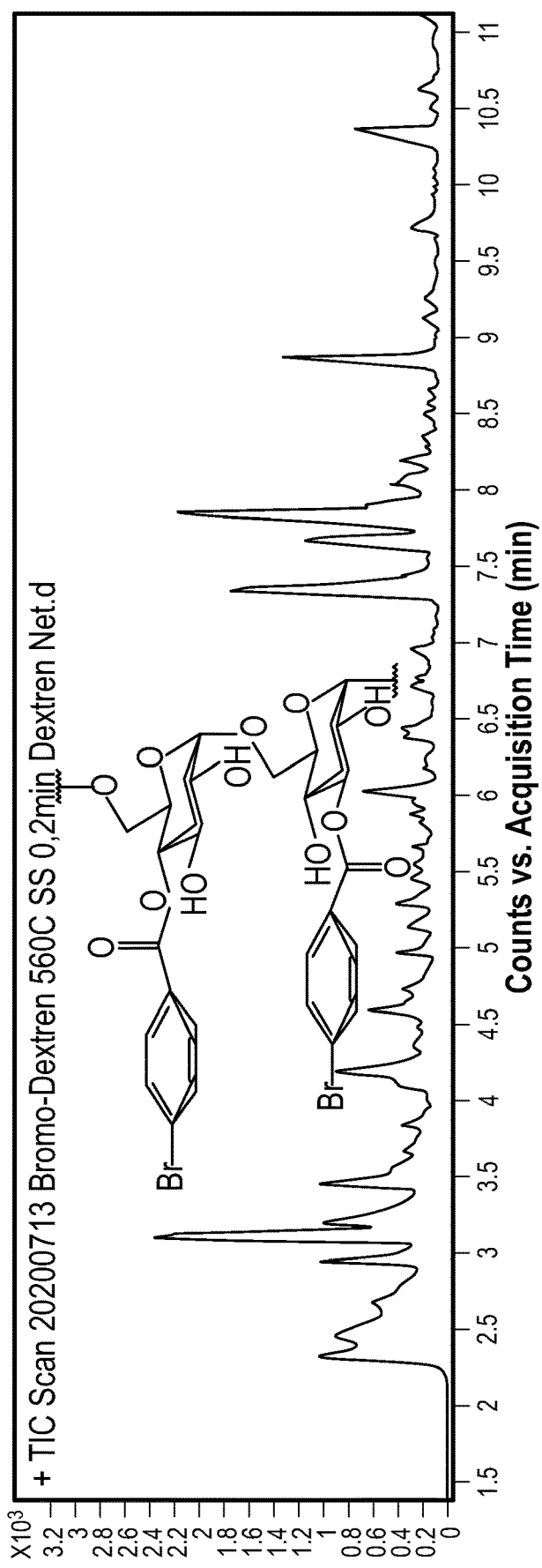
FIGS. 13A-B show the pyrolysis gas chromatography-mass spectrometry (Py GC-MS) analysis and the mass spectra of dextran 4-bromobenzoate (DBB), which is a degradable polymeric additive, according to one or more embodiments.
Figure 13B:
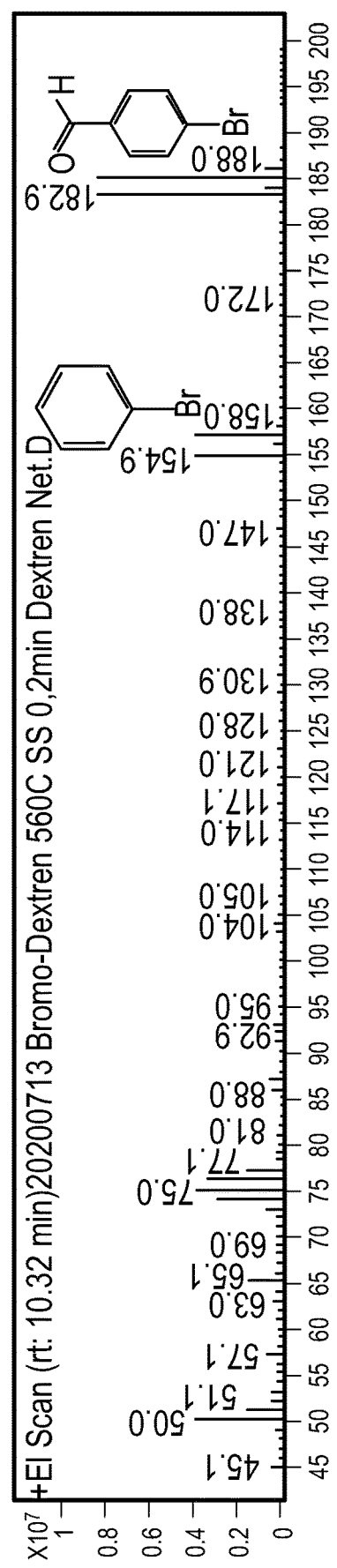

FIGS. 13A-B show the pyrolysis gas chromatography-mass spectrometry (Py GC-MS) analysis and the mass spectra of dextran 4-bromobenzoate (DBB), which is a degradable polymeric additive, according to one or more embodiments. FIG. 10A depicts the Py GC-MS analysis of DBB. FIG. 13B is the corresponding mass spectra for DBB. The mass spectra show the presence of 4-bromobenzene and 4-bromobenzaldehyde cleaved from the polymer backbone after pyrolysis. Several changes in the run made for DBB are noted. A trace sample of dextran-4-bromobenzoate was loaded into a Frontier model PY-30305 pyrolizer linked to an Agilent 7000D QQQ system. The sample was flash pyrolyzed at 550° C. for 0.2 min and the column used for separation was an Agilent HP-5 ms UI column with the following specifications: 30 m length, 0.25 mm inner diameter (ID), and 0.25 mm film. The set temperature of the back inlet was 280° C. with a split ratio of 20 to 1 and a split flow of 22 mL/min. The flow rate of the carrier He gas through the column was 1.1 mL/min at a constant flow mode. The oven temperature started at 75° C. and increased to 150° C. at 10° C./min, then increased to 325° C. at 50° C./min, and finally was held at 325° C. for 7 minutes. No post run condition was applied.

The mass spectrometer used an electron ionization (EI) source set to MS1 scan mode. In this mode, the ions passed from the first quadrupole to the detector while the collision cell and second quadrupole remained inactive. The MS scanned each sample at a mass range of 45 to 200 with a gain factor of 10 and a threshold set to 100.

Starch Esters Hydrolysis Study

Solutions at pH 9 and 13 were made by preparing 0.01 M (molar) and 0.5 M sodium hydroxide solutions, respectively. The pH was monitored by a pH-meter. Aliquots of starch 4-chlorobenzoate (SCB, 100 mg) were separately prepared and transferred into 6 small vials. Milli-Q water (10.00 mL) was added into 3 vials each and the solution of pH 9 was added into each of the vials. Aliquots of starch 4-bromobenzoate (SBB, 100 mg) and starch 4-fluorobenzoate (SFB, 100 mg) were separately prepared and transferred in 2 small vials. The pH 13 solution (10.00 mL) was added to each of the vials. All 8 vials were sealed with caps and placed into a 95° C. oven. SCB samples with Milli-Q water (MQ) were tested after 3, 6, and 13 days, and SCB samples with pH 9 solution were tested after 6, 15, and 18 days. SBB and SFB samples with pH 13 was taken out of the oven after 3 days (Table 1). The solid was separated by centrifugation and washed with ethanol and acetone before vacuum drying.

TABLE 1

Samples prepared for hydrolysis test

| Starch Ester | Solution | Time |
|---|---|---|
| SCB | H$_2$O | 3 days |
| SCB | H$_2$O | 6 days |
| SCB | H$_2$O | 13 days |
| SCB | pH = 9 | 6 days |
| SCB | pH = 9 | 15 days |
| SCB | pH = 9 | 18 days |
| SBB | pH = 13 | 3 days |
| SFB | pH = 13 | 3 days |

To confirm that the ester functionalized polymers can be hydrolyzed, two synthesized starch esters—SBB and SFB—are treated under strong basic conditions (sodium hydroxide aqueous solution, pH 13) at 95° C. for 3 days. After 3 days, the color of solutions changed from transparent to dark yellow. The pH of the solution decreased from 13.0 to 11.2. The aqueous phase was freeze-dried and then analyzed by $^1$H NMR analysis in D$_2$O.

Figure 14A:
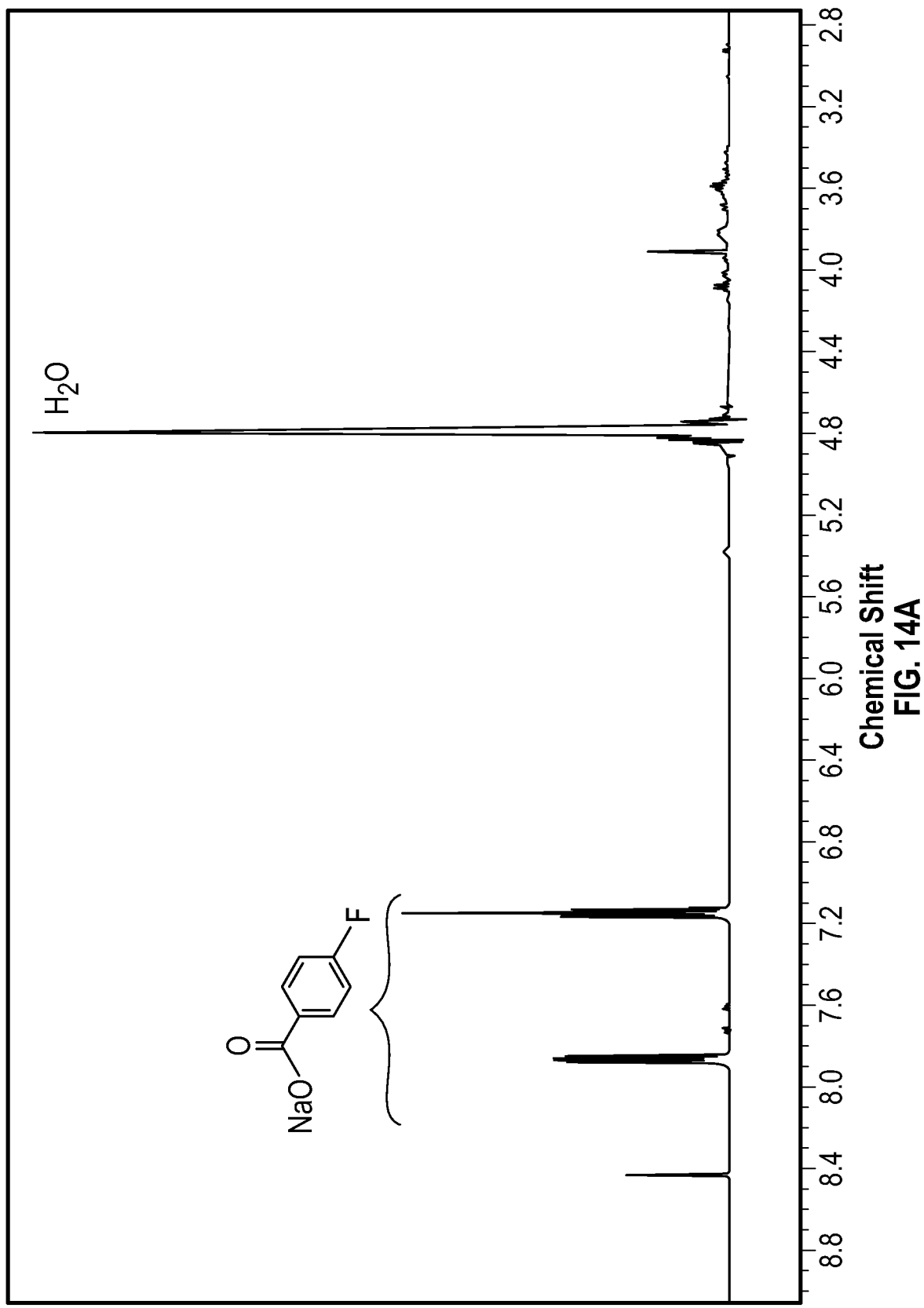
FIG. 14A depicts $^1$H NMR spectra of starch 4-fluorobenzoate (SFB), a degradable polymeric additive, which is according to one or more embodiments, after the degradation study.

FIG. 14A depicts $^1$H NMR spectra of starch 4-fluorobenzoate (SFB), which is a degradable polymeric additive, according to one or more embodiments, after the degradation study. The NMR spectrum of the aqueous solution confirms degradation of the degradable polymeric additive. The NMR spectrum of the aqueous phase SFB degradation study displays the narrow and sharp peaks from the aromatic protons of 4-fluorobenzoic sodium salt, suggesting the breakage of the ester bonds and formation of the carboxylic salt. Peaks found in the range of 3.2 to 5.6 ppm are attributed to the soluble starch and glucose formed due to breakage of glycosidic linkages.

The change of color, pH, and detection of formed substituted benzoic sodium salt confirms that degradation of the degradable polymeric additives occurred. Additionally, the weight of the insoluble solid decreases from 100 mg to less than 15 mg.

Figure 14B:
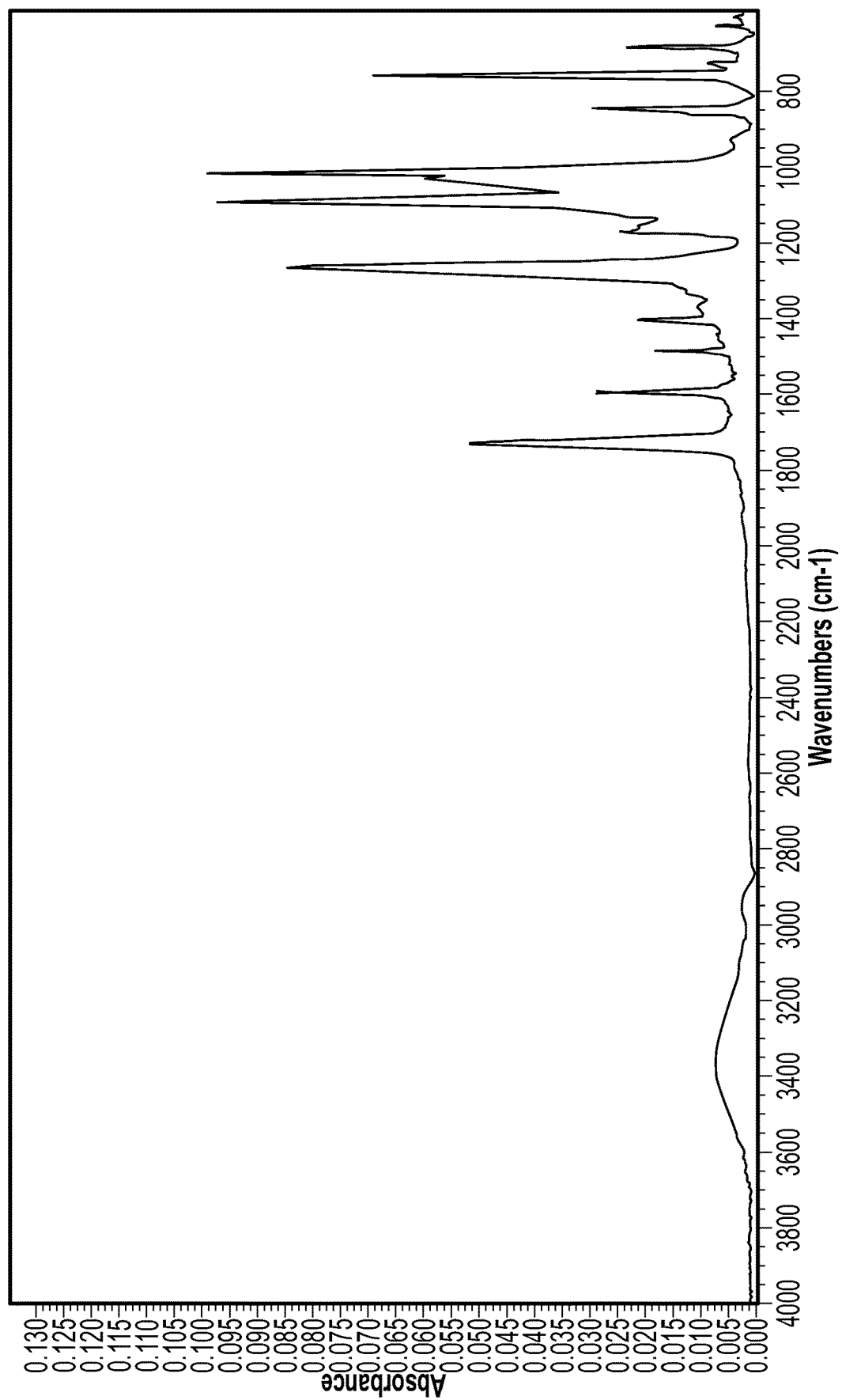
FIG. 14B depicts FT-IR spectra of starch 4-fluorobenzoate (SFB), which is a degradable polymeric additive, which is according to one or more embodiments, after the degradation study.

FIG. 14B depicts FT-IR spectra of starch 4-fluorobenzoate (SFB), which is a degradable polymeric additive, according to one or more embodiments, after the degradation study. The FT-IR spectrum of the remaining solid is almost identical to the starch esters, indicating that the remaining solid is the unhydrolyzed starch esters. Although the reaction was not completed, a significant conversion rate (over 85%, assuming the solid is the unreacted material and aqueous phase is the hydrolyzed product) was observed.

After confirming that polysaccharide esters can be hydrolyzed under strong basic conditions, cleavage of the ester bonds in water-based mud at neutral water and pH 9.0 was investigated.

Figure 16:
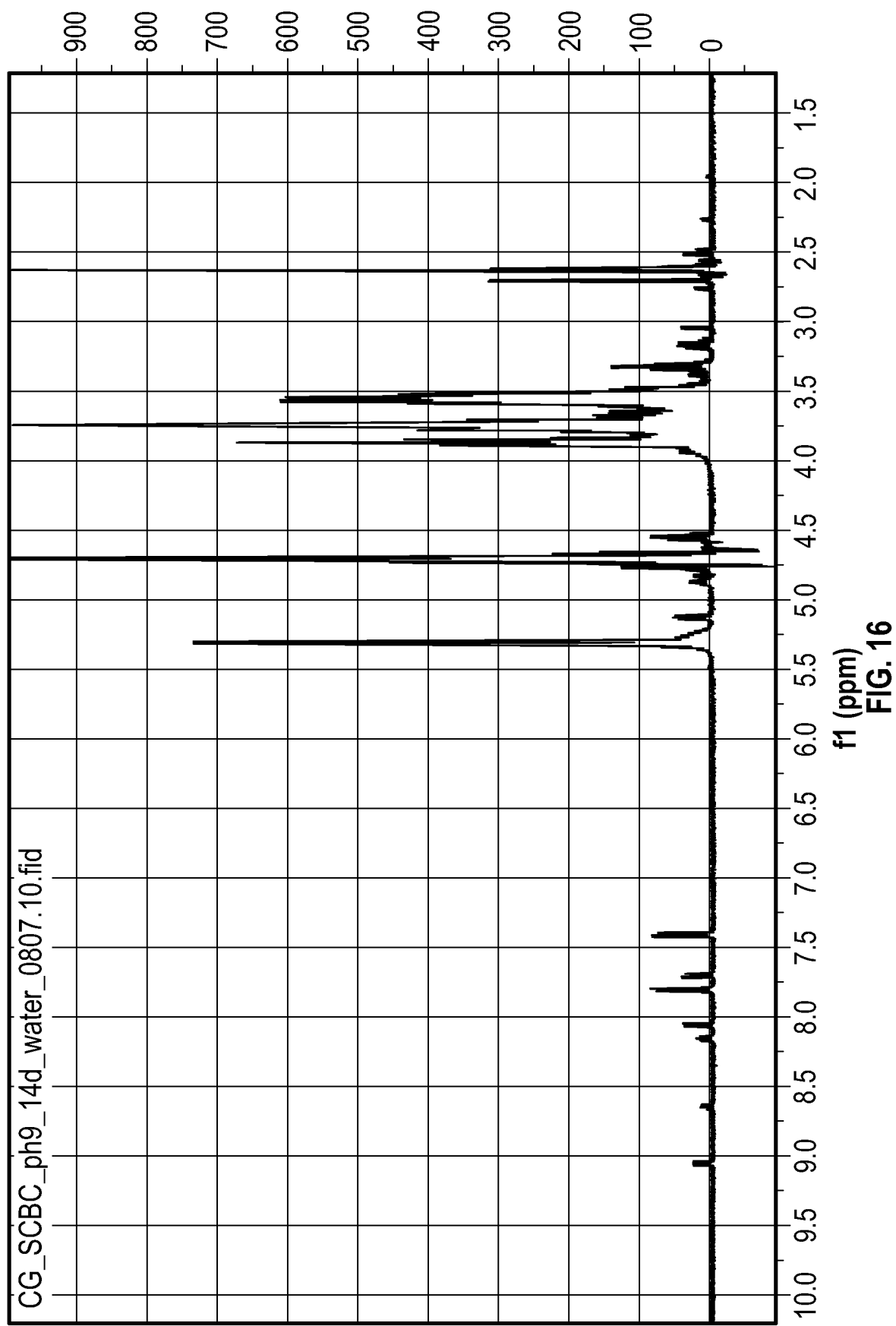
FIG. 16 depicts the $^1$H NMR spectrum of starch 4-chlorobenzene (SCB), which is a degradable polymeric additive, according to one or more embodiments, after degradation at pH 9 for 15 days.

SCB was treated with Milli-Q water and a pH 9 solution for a variable number of days (details are found in Table 1). Analysis of the hydrolyzed product under mild pH condition, as one may expect, take longer to complete. The pH of the aqueous phase decreased from 9.0 to 4.2, indicating the formation of a carboxylic acid. The aqueous phase was analyzed by freeze-drying and the solid phase was directly analyzed by FT-IR. An FT-IR spectrum of the obtained solid after degradation in MQ water for 3 days, 6 days, and 13 days appeared similar to the FT-IR spectrum in FIG. 16. FIG. 16 depicts the $^1$H NMR spectrum of starch 4-chlorobenzene (SCB), which is a degradable polymeric additive, according to one or more embodiments, after degradation at pH 9 for 15 days.

The majority of the solid was found to be insoluble DMSO-d$_6$, even upon heating. However, a small portion was soluble in DMSO-d$_6$ and was analyzed by NMR. The solubility change compared to the starting SCB may be attributed to the hydrolysis of the branch chain of the starch.

Figure 15A:
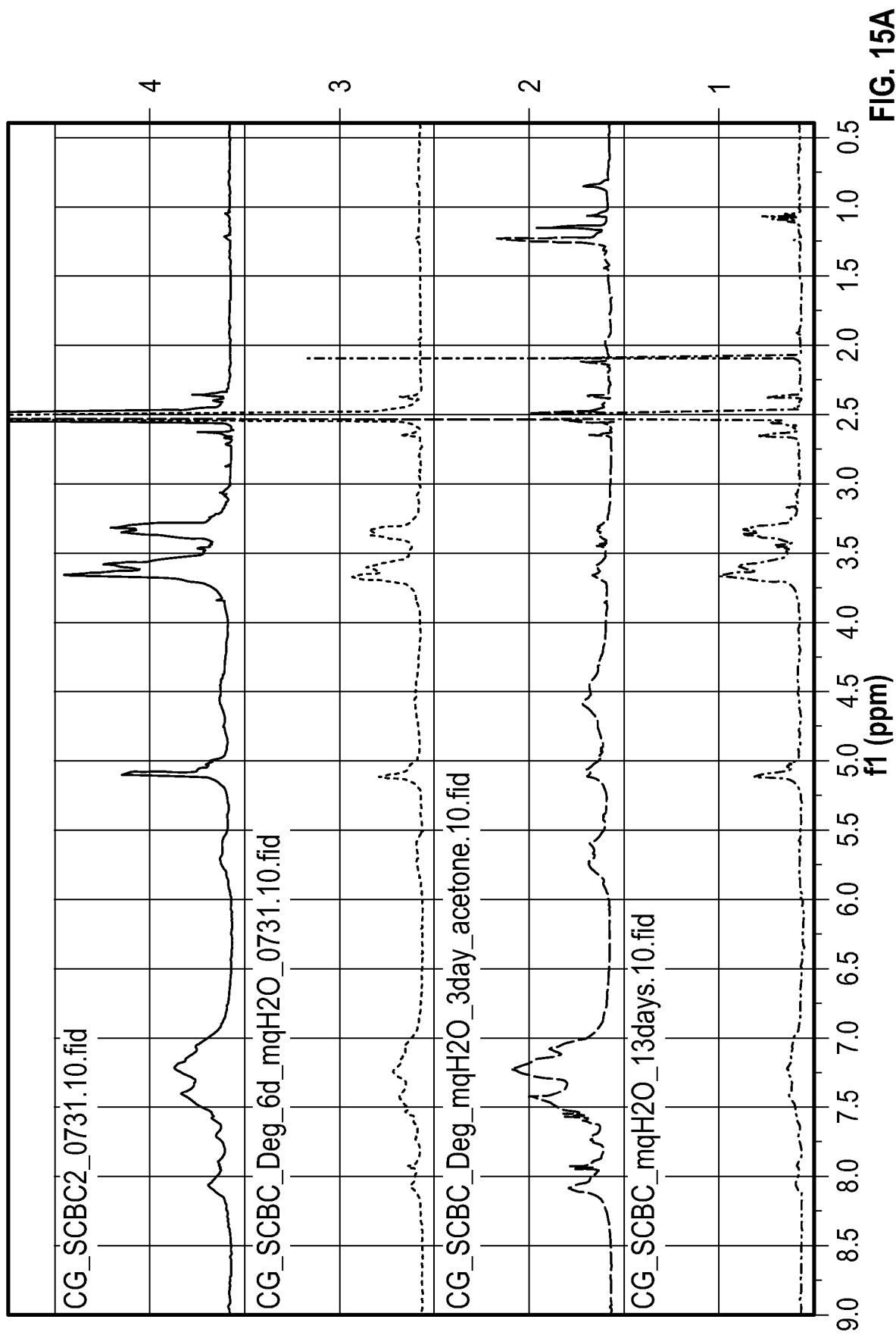
FIG. 15A depicts the $^1$H NMR spectra of starch 4-chlorobenzene (SCB), which is a degradable polymeric additive, according to one or more embodiments, after degradation in neutral pH water.

FIG. 15A depicts the $^1$H NMR spectra of starch 4-chlorobenzene (SCB), which is a degradable polymeric additive, according to one or more embodiments, after degradation in neutral pH water. NMR analysis of the soluble fraction of the solids indicates that there is almost no change after 3 days and 6 days. However, after 13 days (line 1 of FIG. 15A), hydrolyzed starch can be detected as the intensity of the aromatic region decreases. The pH change and detection of the hydrolyzed polymer indicates that hydrolysis occurred, although a FT-IR analysis indicated that the extent of hydrolysis was small.

Degradation at pH 9 shows a similar result, but the degradation occurs faster than in MQ water. Similar methods as previously used were performed to analyze the extent of degradation after 6 days, 15 days, and 18 days. Similarly, no observed change in an FT-IR spectrum was detected. pH decreased from 9.0 to 4.0.

Figure 15B:
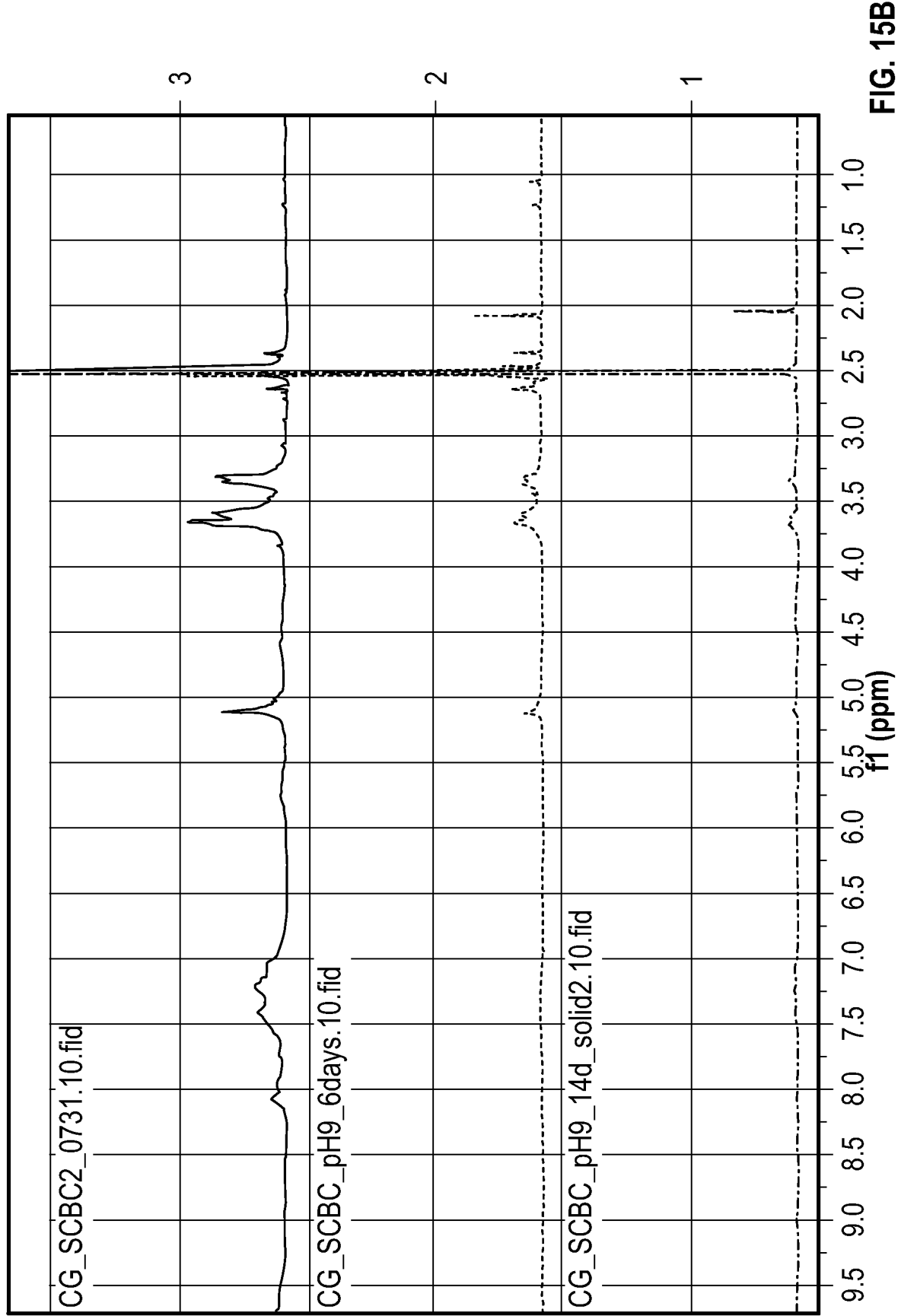
FIG. 15B depicts the $^1$H NMR spectra of starch 4-chlorobenzene (SCB), which is a degradable polymeric additive, according to one or more embodiments, after degradation in pH 9 water.

FIG. 15B depicts the $^1$H NMR spectra of starch 4-chlorobenzene (SCB), which is a degradable polymeric additive, according to one or more embodiments, after degradation in pH 9 water. NMR analysis of the aqueous phase of SCB degradation at pH 9 after 15 days revealed the substituted benzoic acid signal around 7.0 to 8.5 ppm, indicating the hydrolysis reaction occurred. NMR analysis of the solid confirmed that the degradation occurred after 6 days. Similarly, it was observed that the pH changed and hydrolyzed polymer was detected, but an overall change in a FT-IR spectra was not significant. FIG. 13 depicts the $^1$H NMR spectrum of starch 4-chlorobenzene (SCB), which is a degradable polymeric additive, according to one or more embodiments, after degradation at pH 9 for 15 days. Evidence points to the hydrolysis of starch esters occurring, but a longer reaction period appears to be favorable to observe full degradation.

Unless defined otherwise, all technical and scientific terms used have the same meaning as commonly understood by one of ordinary skill in the art to which these systems, apparatuses, methods, processes, and compositions belong.

The singular forms "a," "an," and "the" include plural referents, unless the context clearly dictates otherwise.

As used here and in the appended claims, the words "comprise," "has," and "include" and all grammatical variations thereof are each intended to have an open, non-limiting meaning that does not exclude additional elements or steps.

When the word "approximately" or "about" and variations thereof are used, this term may mean that there can be a variance in value of up to ±10%, of up to 5%, of up to 2%, of up to 1%, of up to 0.5%, of up to 0.1%, or up to 0.01%.

The term "substantially" and variations thereof as used refers to a majority of, or mostly, as in at least about 50%, 60%, 70%, 80%, 90%, 95%, 96%, 97%, 98%, 99%, 99.5%, 99.9%, 99.99%, or at least about 99.999% or more Ranges may be expressed as from about one particular value to about another particular value, inclusive. When such a range is expressed, it is to be understood that another embodiment is from the one particular value to the other particular value, along with all particular values and combinations thereof within the range.

Although only a few example embodiments have been described in detail, those skilled in the art will readily appreciate that many modifications are possible in the example embodiments without materially departing from this disclosure. All modifications of one or more disclosed embodiments are intended to be included within the scope of this disclosure as defined in the following claims. In the claims, means-plus-function clauses are intended to cover the structures previously described as performing the recited function and not only structural equivalents, but also equivalent structures. It is the express intention of the applicant not to invoke 35 U.S.C. § 112(f) for any limitations of any of the claims, except for those in which the claim expressly uses the words 'means for' together with an associated function.

It is noted that one or more of the following claims utilize the term "where" or "in which" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising." For the purposes of defining the present technology, the transitional phrase "consisting of" may be introduced in the claims as a closed preamble term limiting the scope of the claims to the recited components or steps and any naturally occurring impurities. For the purposes of defining the present technology, the transitional phrase "consisting essentially of" may be introduced in the claims to limit the scope of one or more claims to the recited elements, components, materials, or method steps as well as any non-recited elements, components, materials, or method steps that do not materially affect the novel characteristics of the claimed subject matter. The transitional phrases "consisting of" and "consisting essentially of" may be interpreted to be subsets of the open-ended transitional phrases, such as "comprising" and "including," such that any use of an open-ended phrase to introduce a recitation of a series of elements, components, materials, or steps should be interpreted to also disclose recitation of the series of elements, components, materials, or steps using the closed terms "consisting of" and "consisting essentially of." For example, the recitation of a composition "comprising" components A, B, and C should be interpreted as also disclosing a composition "consisting of" components A, B, and C as well as a composition "consisting essentially of" components A, B, and C. Any quantitative value expressed in the present application may be considered to include open-ended embodiments consistent with the transitional phrases "comprising" or "including" as well as closed or partially closed embodiments consistent with the transitional phrases "consisting of" and "consisting essentially of." The words "comprise," "has," and "include" and all grammatical variations thereof are each intended to have an open, non-limiting meaning that does not exclude additional elements or steps.

What is claimed is:

1. An altered drilling mud, comprising:
   a base fluid; and
   a degradable polymeric additive comprises a tracer functional group that is bonded to a base polymeric component by a hydrolysable covalent bond, where the base polymeric component is a polysaccharide and where the tracer functional group is a combination of at least one halogen-containing functional group and a substituted heterocyclic aromatic group, wherein the at least one halogen-containing functional group is derived from a halogenated aromatic compound.

2. The altered drilling mud of claim 1, where the hydrolysable covalent bond is selected from the group consisting of an ester, amide, ether, thioether, or a thioester bond.

3. The altered drilling mud of claim 1, where the halogenated aromatic compound is selected from the group consisting of 4-fluorobenzoate, 4-chlorobenzoate, 4-bromobenzoate, and combinations thereof.

4. The altered drilling mud of claim 1, where the polysaccharide is selected from the group consisting of starch, cellulose, dextran, xanthan gum, and combinations thereof.

5. The altered drilling mud of claim 1, where an amount of degradable polymeric additive present in the altered drilling mud is in a range of from about 0.0001 to 5 wt. % (weight percent).

6. The altered drilling mud of claim 1, where the altered drilling mud has a funnel viscosity in a range of from about 40 to 150 seconds.

7. The altered drilling mud of claim 1, where the base fluid of the altered drilling mud comprises water, petroleum, or a fraction of petroleum.

8. A method of using a degradable polymeric additive, comprising:
   introducing an amount of the degradable polymeric additive into a drilling fluid to form an altered drilling fluid;
   introducing the altered drilling fluid into a wellbore;
   recovering an associated wellbore cutting from a depleted drilling fluid; and
   detecting the presence of the degradable polymeric additive associated with the associated wellbore cutting,
   where the degradable polymeric additive comprises a tracer functional group that is bonded to a base polymeric component by a hydrolysable covalent bond, where the base polymeric component is a polysaccharide, and where the tracer functional group is a combination of at least one halogen-containing functional group and a substituted heterocyclic aromatic group, wherein the at least one halogen-containing functional group is derived from a halogenated aromatic compound.

9. The method of claim 8, where the hydrolysable covalent bond is selected from the group consisting of an ester, amide, ether, thioether, or a thioester bond.

10. The method of claim 8, where the polysaccharide is selected from the group consisting of starch, cellulose, dextran, xanthan gum, and combinations thereof.

11. The method of claim 8, further comprising detecting the presence of the degradable polymer additive in the depleted drilling fluid.

12. The method of claim 8, further comprising treating the depleted drilling fluid to degrade any remaining degradable polymer additive in the depleted drilling fluid.

* * * * *